United States Patent
Ward et al.

(10) Patent No.: US 11,172,839 B2
(45) Date of Patent: Nov. 16, 2021

(54) ESTIMATION OF PERIPHERAL VASCULAR RESISTANCE USING A MINIATURE PIEZOELECTRIC SENSOR

(71) Applicant: THE REGENTS OF THE UNIVERSITY OF MICHIGAN, Ann Arbor, MI (US)

(72) Inventors: Kevin R. Ward, Superior Township, MI (US); Sardar Ansari, Richmond, VA (US); Lu Wang, Ann Arbor, MI (US); Kayvan Najarian, Northville, MI (US); Kenn Oldham, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 147 days.

(21) Appl. No.: 16/344,671

(22) PCT Filed: Oct. 25, 2017

(86) PCT No.: PCT/US2017/058365
§ 371 (c)(1),
(2) Date: Apr. 24, 2019

(87) PCT Pub. No.: WO2018/081314
PCT Pub. Date: May 3, 2018

(65) Prior Publication Data
US 2020/0054221 A1 Feb. 20, 2020

Related U.S. Application Data

(60) Provisional application No. 62/412,571, filed on Oct. 25, 2016.

(51) Int. Cl.
*A61B 5/0205* (2006.01)
*A61B 5/0295* (2006.01)
(Continued)

(52) U.S. Cl.
CPC ........ *A61B 5/0295* (2013.01); *A61B 5/02007* (2013.01); *A61B 5/02255* (2013.01); *A61B 5/1455* (2013.01); *A61B 2562/0247* (2013.01)

(58) Field of Classification Search
CPC ..... A61B 5/0295; A61B 5/05; A61B 5/02255; A61B 5/0205
(Continued)

(56) References Cited

U.S. PATENT DOCUMENTS

| 6,413,223 B1 | 7/2002 | Yang et al. |
| 2003/0009101 A1* | 1/2003 | Sunagawa .......... A61B 5/02007 600/437 |

(Continued)

OTHER PUBLICATIONS

European Application No. 17864198, Extended European Search Report, dated Mar. 16, 2020.
(Continued)

*Primary Examiner* — Lynsey C Eiseman
*Assistant Examiner* — Jessica L Mullins
(74) *Attorney, Agent, or Firm* — Marshall, Gerstein & Borun LLP

(57) ABSTRACT

A wearable assembly has a pulse plethysmography (PPG) sensor and a piezoelectric pressure sensor and is attachable to a patient's finger or other area corresponding to a peripheral vascular region, and further includes a signal processor configured to monitor blood flow dependent measurements and pressure measurements over time, comparing these measurements to determine properties of the vascular region, such as vascular resistance of a blood vessel, vascular radius of the blood vessel, vascular stiffness of the vascular region, blood pressure, and/or cardiac vascular power. The signal processor may apply a hysteresis comparison of the sensor outputs, e.g., using an elliptical model, and in some examples may apply an extended Kalman filter for optimizing output of the vascular region properties.

21 Claims, 35 Drawing Sheets

(51) Int. Cl.
*A61B 5/02* (2006.01)
*A61B 5/0225* (2006.01)
*A61B 5/1455* (2006.01)

(58) Field of Classification Search
USPC .................................................. 600/301, 324
See application file for complete search history.

(56) References Cited

U.S. PATENT DOCUMENTS

| | | |
|---|---|---|
| 2006/0074322 A1 | 4/2006 | Nitzan |
| 2008/0039731 A1 | 2/2008 | McCombie et al. |
| 2012/0123232 A1 | 5/2012 | Najarian et al. |
| 2014/0066732 A1 | 3/2014 | Addison et al. |
| 2014/0081098 A1* | 3/2014 | Cohrs ................... A61B 5/029 |
| | | 600/324 |
| 2015/0305632 A1 | 10/2015 | Najarian et al. |
| 2016/0198955 A1 | 7/2016 | Fortin |

OTHER PUBLICATIONS

International Application No. PCT/US17/58365, International Search Report and Written Opinion, dated Jan. 3, 2018.
Olufsen et al., Blood pressure and blood flow variation during postural change from sitting to standing: model development and validation, J. Appl. Physiol., 99(4):1523-37 (Oct. 2005).
Wang et al., Estimation of peripheral artery radius using non-invasive sensors and Kalman filtering of local dynamics, 2017 American Control Conference.
Wang et al., Non-invasive vascular resistance monitoring with a piezoelectric sensor and photoplethysmogram, Sensors and Actuators A: Physical, 263:198-208 (Jun. 2017).

* cited by examiner

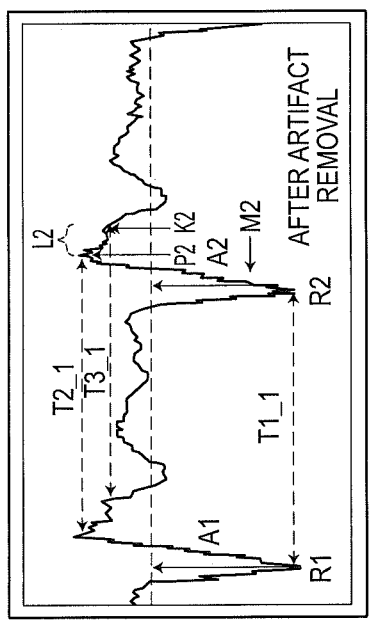
FIG. 7A
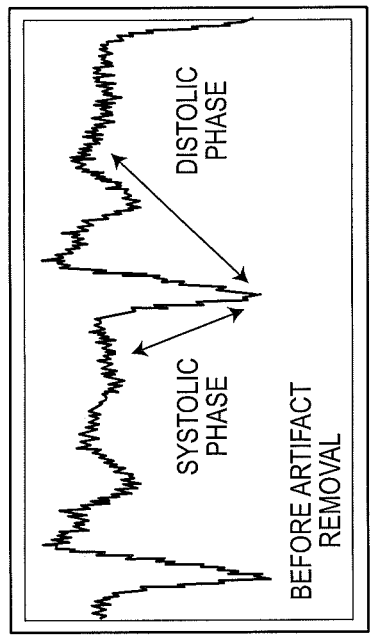
FIG. 7B

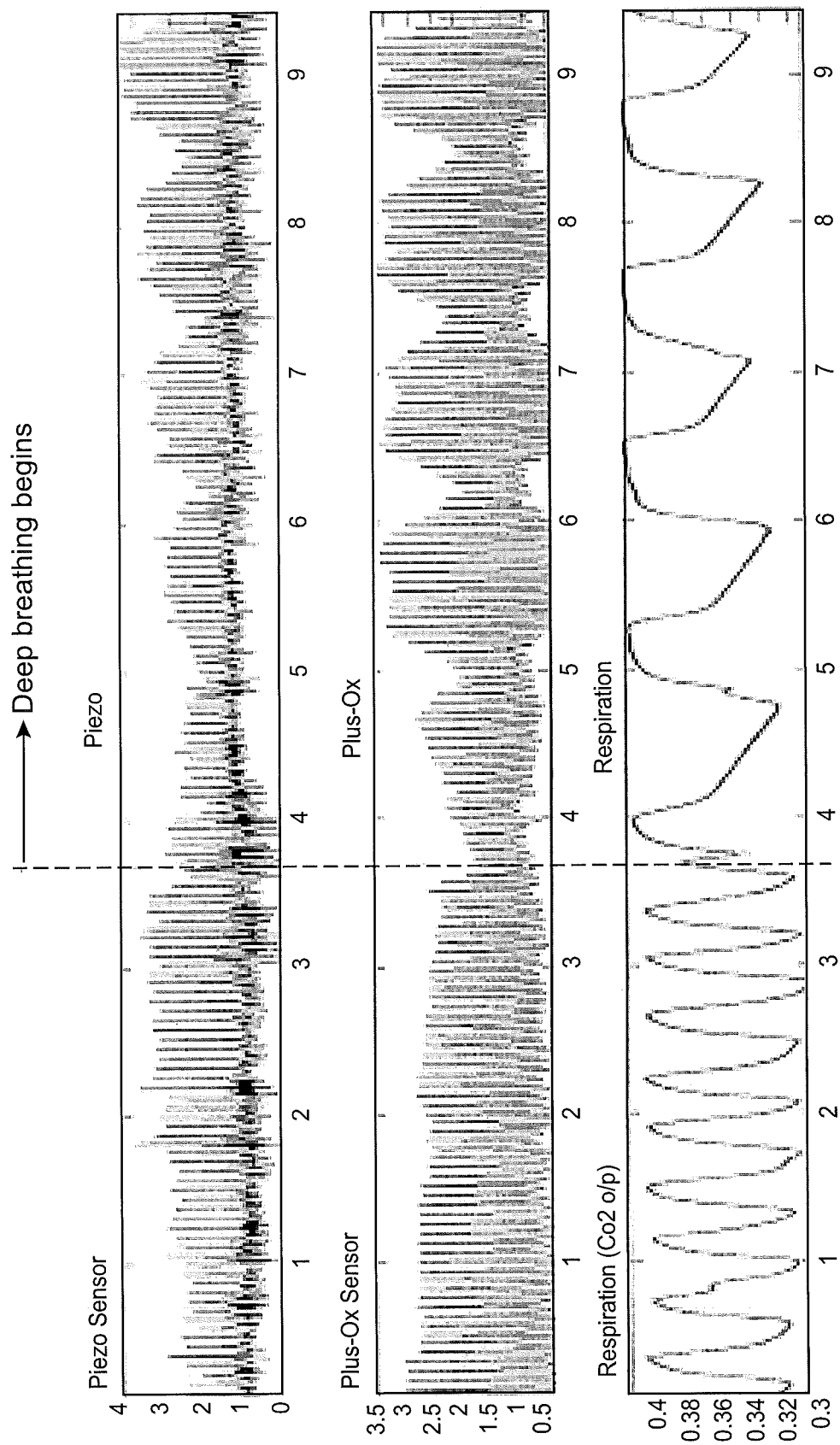
FIG. 13E Deep Breathing

Fast Breathing

BP Cuff inflation and deflation

ESTIMATION OF PERIPHERAL VASCULAR RESISTANCE USING A MINIATURE PIEZOELECTRIC SENSOR

CROSS-REFERENCE TO RELATED APPLICATIONS

This application claims priority to U.S. Provisional Application No. 62/412,571, entitled Estimation of Peripheral Vascular Resistance Using a Miniature Piezoelectric Sensor, and filed Oct. 25, 2016, which is incorporated herein by reference in its entirety. This application further claims priority to PCT Patent Application No. PCT/US2017/058365, entitled Estimation of Peripheral Vascular Resistance Using a Miniature Piezoelectric Sensor, and filed on Oct. 25, 2017, which is incorporated herein by reference in its entirety.

STATEMENT OF GOVERNMENT SUPPORT

This invention was made with government support under CMMI1562254 awarded by the National Science Foundation. The government has certain rights in the invention.

FIELD OF THE DISCLOSURE

The present disclosure relates to wearable health related monitors and, more particularly, to techniques for gathering blood pressure, flow data, and/or other cardiovascular variables via a wearable sensor assembly.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Cardiovascular diseases are the most common cause of death worldwide. Currently, there are no effective portable and low-powered devices or systems that can be used for the non-invasive continuous monitoring of the cardiovascular system. The monitoring and treatment of medical and surgical conditions such as sepsis, congestive heart failure, hypertension, trauma, and other acute and chronic diseases could tremendously benefit from devices that allow direct or indirect continuous monitoring of important cardiovascular parameters in a nonintrusive manner. For example, monitoring cardiovascular parameters such as blood pressure waveform analysis (BPWA) and derivatives such as pulse pressure variability (PPV), or heart rate complexity changes such as heart rate variability (HRV) or respiratory rate (RR), or event dynamic changes in arterial vessel wall stiffness and the like could lead to effective measures for analyzing physiological conditions. That's because, at least in part, features extracted from these cardiovascular parameters have been shown to be highly correlative with a number of physiological conditions. Therefore, an effective technique for monitoring could provide caregivers with a variety of valuable clinical decision-making tools.

Yet, current techniques for continuous blood pressure (BP) and blood pressure waveform measurement are problematic. The techniques are invasive and confined to stationary complex clinical settings such as the intensive care unit (ICU). Hence, the techniques are not suitable for a wide range of applications, including personal healthcare monitoring.

Non-continuous monitoring systems have been proposed, but these too are problematic. Some of these non-continuous monitoring systems are relatively portable and non-invasive. However, they fail to provide the true waveform data of blood pressure and vascular tone (i.e., the degree of constriction experienced by a blood vessel relative to its maximally dilated state). Instead, these conventional techniques, whether from limitations in sensor sensitivity or limitations in data analysis, produce a reduced waveform data. They are incapable of producing true waveforms resulting from vascular wall movement or motion that are reflective of vascular tone, which are, as we show with the novel techniques described below, highly informative and rich with extracted clinically-useful information. Moreover, the majority of current noninvasive systems are cumbersome, since inflation of their mechanical cuff (or balloon) obstructs the normal everyday activities of life for the users. The systems are not usually wearable; and the information they provide lacks the frequency and granularity in which to take advantage of advances in the fields of signal processing and artificial intelligence. Further still, conventional noninvasive systems have been demonstrated to become inaccurate when patient physiology is labile, as occurs in critical states like hemorrhage or sepsis.

Another limitation of conventional systems is their inability to accurately measure vascular resistance. The state of a person's peripheral arteries is known to be a key physiological indicator of their body's response to both acute and chronic medical conditions. The body's vascular tone, or constriction of the arteries relative to a maximally dilated state, is a direct indicator of the body's response to cardiovascular stress. Peripheral arterial constriction or dilation is also the dominant factor in determining the body's systemic vascular resistance (SVR), which is the resistance felt by the heart in forcing blood through the circulatory system. SVR is a major means of compensation to maintain physiological homeostasis. Rapid changes in vascular tone and SVR are known to be associated with important physiological situations, such as shock (sepsis, traumatic, etc.), post-surgical recovery, and dialysis.

Yet, despite the potential value of being able to continuously and rapidly monitor vascular tone and SVR, existing technology for acquiring this information is severely limited, especially when considering continuous, non-invasive technologies. Peripheral artery diameter can be directly measured only through biomedical imaging, typically ultrasound, which is not available on a continuous basis or in most care settings. Acoustic techniques have also been proposed for measuring SVR, but with limited results. The current gold standard for SVR measurement is invasive monitoring of cardiac output and arterial pressure through catheterization, available only in intensive care settings, and not universally even then. Researchers have also proposed improvements on vascular resistance measurements by applying more complex models to aortic flow data. Non-invasive systems for estimating cardiac output, and from there inferring SVR, have been commercialized based on electrical cardiometry and whole body bioimpedance. However, these techniques track SVR only weakly, since central venous pressure is not measured, and are also unavailable outside of acute medical care settings.

Some have proposed methods for estimating SVR and vascular tone using simpler instruments. Prior attempts have generally relied on photo plethysmograph (PPG) data, which tracks changes in artery volume within short-term pulse cycles. Timing of reflection waves as extracted from PPG data has been reported to indicate changes in peripheral arterial resistance, but this was only verified through basic correlations with expected trends among hypertension subjects, not individualized tracking. Methods for extracting SVR from multiple regression of PPG waveform data points have been derived by machine learning techniques, but SVR estimation error ranged from 15%-100% for most subjects. Evaluating a vascular tone index by matching models for arterial dynamics to pulse transit time (PTT) and blood pressure (BP) measurements has also been proposed. However, the results could at most be correlated with risk factors for high SVR, rather than to SVR itself. Another report showed PTT correlation with SVR over time, but only for two individual cases. Estimates of cardiac output and vascular resistance have also been suggested based on ECG and BP cuff data, and used in tracking response to physical activity, but these are recognized as only approximate measures. None of the proposed techniques provide suitable solutions.

In light of these limitations and given the increased need for health care delivery models, there is a strong need to develop low-cost wearable monitoring systems that can span from the home to the hospital and that are capable of providing deeper physiologic information that help both health care providers and patients manage disease states in a more real-time fashion. Furthermore, there is a need for tracking SVR in real time using techniques that that do not require expensive and service-limiting acute medical care facilities to implement.

SUMMARY OF THE INVENTION

The present techniques include devices and techniques for estimating systemic vascular resistance (SVR), vascular tone, blood pressure, and cardiac-vascular power using mountable instruments. The techniques include tracking changes in vascular tone by combining pulse plethysmography (PPG) data, with measurements from an adjacent compliant piezoelectric polymer pressure sensors (e.g., polyvinylidene fluoride "PVDF" sensors). These dual sensors, PPG sensors, and piezoelectric pressure sensors, may be combined in a wearable device, such as finger mountable device.

In some examples, the pressure sensor is mounted onto a finger of a patient. In some examples, the pressure sensor provides a non-invasive piezoelectric arterial pressure sensing with sensors fabricated from PVDF films and a controller configured to perform real-time waveform monitoring for pulse and respiration. In some examples, the pressure sensor may be based on thin-film lead-zirconate titanate (PZT) in a polymer film, or on nanowire-impregnated polymers, and/or amorphous PZT films. The compactness of the present designs allows for accurate tracking of vascular resistance. The pressure seasons may be formed using any number of different transduction modalities, e.g., piezoelectric, resistive, capacitive, combinations thereof, etc., in the present techniques; and these modalities each may be provided in compliant sensing structures to accurate track, in real time, vascular resistance.

In an embodiment, an apparatus comprises: a wearable sensor assembly configured to be attached to a subject at a peripheral vascular region, the wearable sensor assembly comprising: a piezoelectric pressure sensor configured to measure pressure data of the peripheral vascular region, wherein the piezoelectric sensor comprises a piezoelectric electrode structure positioned to measure the pressure data in response to movement of a blood vessel in the peripheral vascular region, and a pulse-oximetry sensor positioned to collect photoplethysmograph derived blood flow data of the blood vessel; and a signal processor configured to receive the pressure data from the piezoelectric pressure sensor, analyze the pressure data and output a pressure value, analyze the collected photoplethysmograph derived blood flow and output a photoplethysmograph blood flow value, using a blood flow model, compare the photoplethysmograph blood flow value with the pressure value, using a hysteresis comparison, and in response to the comparison, extract an indicator of peripheral vascular resistance of the blood vessel, wherein the indicator of peripheral vascular resistance indicates vascular health and condition of the subject.

In an embodiment, to compare the photoplethysmograph blood flow value and the pressure value, in real time, by applying the hysteresis comparison, a signal processor is configured to: develop an elliptical model of the pressure value versus the photoplethysmograph blood flow value; determine for a long chord of the elliptical model, a fixed model radius, Ls; and determine for the long chord of an experimentally obtained elliptical model, a model radius, Le.

In an embodiment, a signal processor is configured to extract an indicator of vascular resistance of the blood vessel based on variation in amplitudes of the pressure value and the photoplethysmograph blood flow value represented by Ls and Le, respectively.

In an embodiment, a signal processor is configured to extract the indicator of vascular resistance of the blood vessel based on variation of the pressure value versus the photoplethysmograph blood flow value using a hysteresis comparison measured by an elliptical model.

In an embodiment, the apparatus includes a self-contained power source of the piezoelectric sensor and/or the photoplethysmography sensor in the wearable sensor assembly.

In an embodiment, a signal processor is external to a wearable sensor assembly and communicatively connected the wearable sensor assembly through a wireless communication network or through an external wired connection.

In an embodiment, a signal processor is configured to determine cardiac vascular power, determining a charge response of the piezoelectric pressure sensor; determining a square of the charge response; and applying a piezoelectric sensor property factor to the square of the charge response, wherein the piezoelectric sensor property factor is a value that compensates for one or more of material properties of the piezoelectric sensor, dimensions of the piezoelectric sensor, an amount of deformation of the piezoelectric sensor, and combinations thereof.

In an embodiment, a signal processor is configured to determine a radius of the blood vessel.

In an embodiment, a wearable sensor assembly further comprises: an additional piezoelectric pressure sensor configured to measure an absolute pressure data of the peripheral vascular region, and a signal processor is configured to receive the absolute pressure data from the additional piezoelectric pressure sensor, compare the absolutely data to the pressure data from the piezoelectric pressure sensor, and determine an absolute blood pressure for the subject.

In an embodiment, a signal processor is further configured to determine an average pulse transit time (PTT) between the piezoelectric pressure sensor and the pulse-oximetry sensor over a sample period, determine if a subsequent PTT deviates by more than a threshold amount from the average PTT, and identify the subsequent PTT and corresponding pressure value and photoplethysmograph blood flow value as noise, if the subsequent PTT deviates by more than a threshold amount from the average PTT.

In an embodiment, a signal processor is further configured to determine an average pulse transit time (PTT) between the piezoelectric pressure sensor and the pulse-oximetry sensor over a sample period, and determine a vascular mechanical stiffness for the blood vessel from the PTT.

In an embodiment, a signal processor is configured to compare the photoplethysmograph blood flow value with the pressure value using a state model, the state model configured to model at least one of physical properties of the wearable sensor assembly, properties of the vascular region, and properties of the blood vessel, apply an extended Kalman filter to the comparison of the photoplethysmograph blood flow value with the pressure value using a state model, and extract vascular radius as the indicator of peripheral vascular resistance of the blood vessel.

In an embodiment, a signal processor is configured to extract an indicator of peripheral vascular radius, vascular stiffness, blood pressure, and/or cardiac vascular power.

In an embodiment, a signal processor is configured to extract an indicator of peripheral vascular radius of the blood vessel, vascular stiffness of the blood vessel, blood pressure, and/or cardiac vascular power in response to a comparison of the photoplethysmograph blood flow value with the pressure value.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 3A illustrates a plot of raw signal data measured by the piezoelectric sensor of FIGS. 2A and 2B, while

FIGS. 7A and 7B illustrate a segment of the raw signal data before and after artifact removal, respectively, where in FIG. 7B, the segment has been analyzed for data extraction, as may be performed in accordance with the signal processor of FIG. 4, in accordance with an example;

DETAILED DESCRIPTION

The present techniques provide devices and methods for measuring and monitoring blood flow dependent measurements over a sensing region of a subject, such as over a finger or other peripheral arterial region. Example devices include wearable sensor devices having two or more sensors of different types. For example, these wearable sensor devices may include a piezoelectric pressure sensor and a pulse-oximetry sensor for measuring blood saturation levels and operating as a pulse plethysmography (PPG) sensor with corresponding output. As used herein, pulse-oximetry sensors refers to any pulse-oximetry sensors and any other suitable biophotonic sensors.

Figure 1:
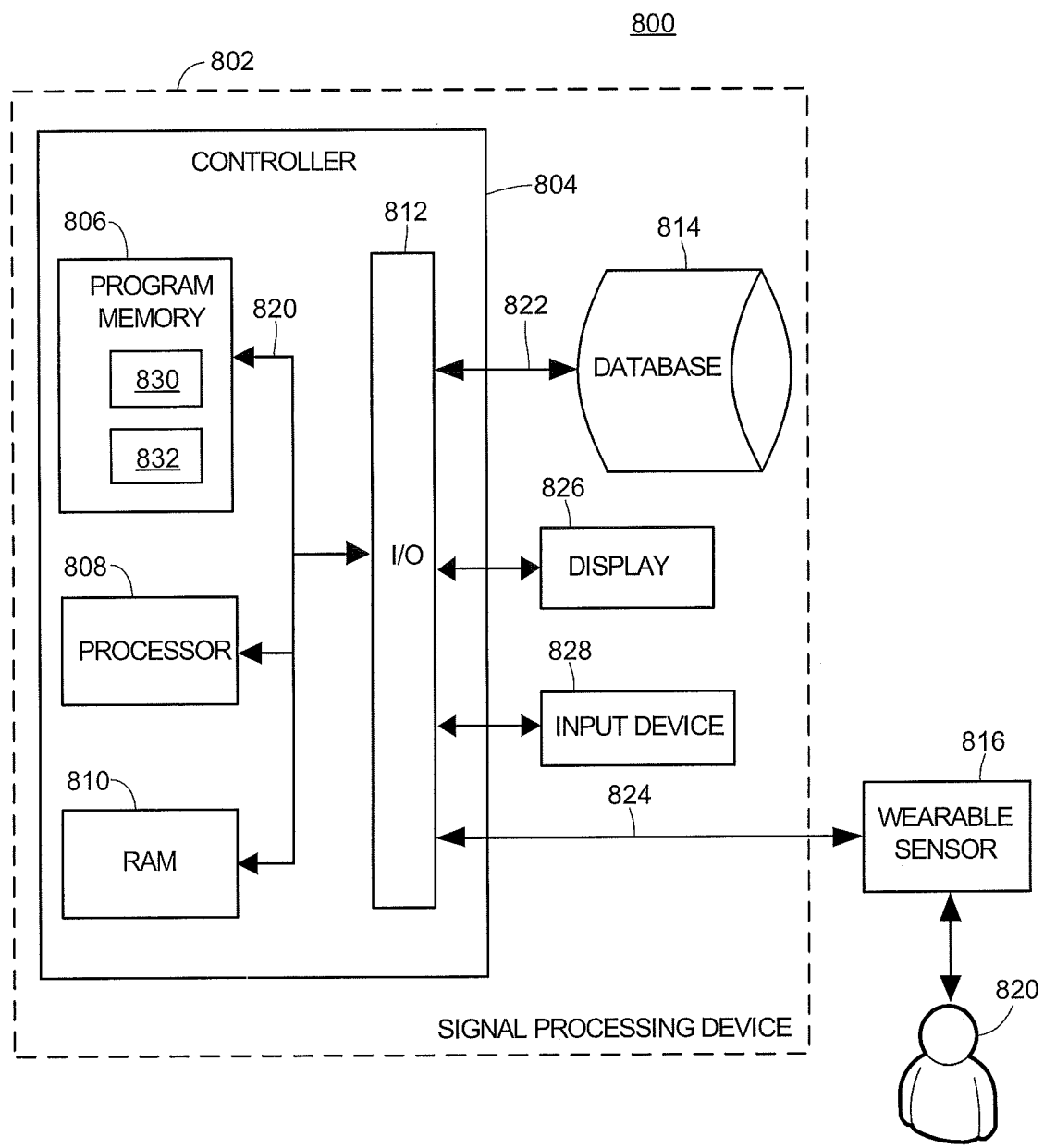
FIG. 1 is a schematic view of an apparatus for measuring raw signal data using a piezoelectric sensor-based device and for extracting physiological conditions from the raw signal data, in accordance with an example.

FIG. 1 is an example block diagram 800 illustrating the various components used in implementing an example embodiment of a piezoelectric cardiovascular monitoring system discussed herein. A signal-processing device 802 (or "signal processor") may be coupled to a patient 820 via one or more wearable sensors 816 (or a "wearable sensor assembly") in accordance with executing the functions of the disclosed embodiments. The signal-processing device 802 may have a controller 804 operatively connected to the database 814 via a link 822 connected to an input/output (I/O) circuit 812. It should be noted that, while not shown, additional databases may be linked to the controller 804 in a known manner. The controller 804 includes a program memory 806, one or more processors 808 (may be called microcontrollers or a microprocessors), a random-access memory (RAM) 810, and the input/output (I/O) circuit 812, all of which are interconnected via an address/data bus 820. It should be appreciated that although only one processor 808 is shown, the controller 804 may include multiple microprocessors 808. Similarly, the memory of the controller 804 may include multiple RAMs 810 and multiple program memories 806. Although the I/O circuit 812 is shown as a single block, it should be appreciated that the I/O circuit 812 may include a number of different types of I/O circuits. The RAM(s) 810 and the program memories 806 may be implemented as semiconductor memories, magnetically readable memories, and/or optically readable memories, for example. A link 824, which may include one or more wired and/or wireless (Bluetooth, WLAN, etc.) connections, may operatively connect the controller 804 to a wearable sensor 816 through the I/O circuit 812. The wearable sensor 816 may be operatively connected to the patient 820. Further details of an example wearable sensor, or wearable sensor assembly, are included in reference to FIG. 2A, FIG. 2B, and FIG. 2C.

The program memory 806 and/or the RAM 810 may store various applications (i.e., machine readable instructions) for execution by the processor 808. For example, an operating system 830 may generally control the operation of the signal-processing device 802 and provide a user interface to the signal-processing device 802 to implement the process 100 described herein. The program memory 806 and/or the RAM 810 may also store a variety of subroutines 832 for accessing specific functions of the signal-processing device 802. By way of example, and without limitation, the subroutines 832 may include, among other things: a subroutine for taking measurements with the wearable sensor 816, a subroutine for filtering measurement (or data) from the wearable sensor 816, a subroutine for performing signal decomposition on raw signal data from the wearable sensor 816, and a subroutine for extracting one or more features of a sensing region from the raw signal data from the wearable sensor 816. The subroutines 832 may also include other subroutines, for example, implementing software keyboard functionality, interfacing with other hardware in the signal-processing device 802, etc. The program memory 806 and/or the RAM 810 may further store data related to the configuration and/or operation of the signal-processing device 802, and/or related to the operation of the one or more subroutines 832. For example, the data may be data gathered by the wearable sensor 816, data determined and/or calculated by the processor 808, etc. In addition to the controller 804, the signal-processing device 802 may include other hardware resources. The signal-processing device 802 may also include various types of input/output hardware such as a visual display 826 and input device(s) 828 (e.g., keypad, keyboard, etc.). In an embodiment, the display 826 is touch-sensitive, and may cooperate with a software keyboard routine as one of the software routines 832 to accept user input. It may be advantageous for the signal-processing device 802 to communicate with a broader medical treatment network (not shown) through any of a number of known networking devices and techniques (e.g., through a commuter network such as an hospital or clinic intranet, the Internet, etc.). For example, the testing apparatus may be connected to a medical records database, hospital management processing system, health care professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

Although depicted as separate entities or components in FIG. 1, it is understood that any or the entire signal processing functionality and/or components of the signal-processing device 802 may be combined with a wearable sensor assembly, such as the wearable sensor 816. In this manner, a wearable sensor may both gather data about the patient 820 and process the gathered data to extract one or more waveform features, as discussed further below.

Also, although depicted as a single component in FIG. 1, the wearable sensor 816 may include multiple of the same type or different types of sensors. For example, the wearable sensor 816 may include both a piezoelectric pressure sensor for measuring raw signal pressure data and a secondary sensor for collecting photoplethysmograph derived blood flow and hemoglobin oxygen saturation data. Generally, the wearable sensor 816 may include one or more piezoelectric sensors or electrodes, as further discussed with reference to FIG. 2A, FIG. 2B, and FIG. 2C. In some examples, the wearable sensor 816 may be implemented with one or more of a variety of other (or secondary) sensors, such as temperature sensors, motion sensors, actigraphy sensors, galvanic skin response sensors, impedance sensors, etc.

In some examples in which the wearable sensor 816 includes a secondary sensor for collecting photoplethysmograph derived blood flow data, the secondary sensor may provide (e.g., to a signal processing computer) a waveform that is flow related. The changes in the waveform may provide information related to the arterial tone at both the site of measure and, in some cases, more centrally. Changes in the waveform from the secondary sensor along with changes in a waveform from the piezoelectric sensor (amplitude, width, time differences in peaks, delta responses to provocative movements such as breathing, volume infusion, etc.) may provide complementary information about the patient as it relates to circulating vascular volumes and vascular tone. Thus, the ability to look at these two signals together allows for determining which components are responsible for changes and as well as how best to favorably affect changes, such as providing medications to tighten or relax arterial wall tone. An example implementation of the wearable sensor 816 as a two-sensor device is shown in FIGS. 14A-14C, 16A, 16B, 17, and 18.

In the example of wearable sensor that further includes a motion sensor, the signal-processing device 802 may collect row motion data and determine changes in motion of the wearable sensor, e.g., in response to changes in the location or orientation of the sensing region and/or of the subject. With this data, the signal-processing device 802 may extract motion artifacts and suppress or even cancel noise in the raw signal data based on that motion data. In some examples, the motion sensor may be implemented as a gyroscopic sensor or an accelerometer imbedded within the wearable sensor 816.

Figure 2A:
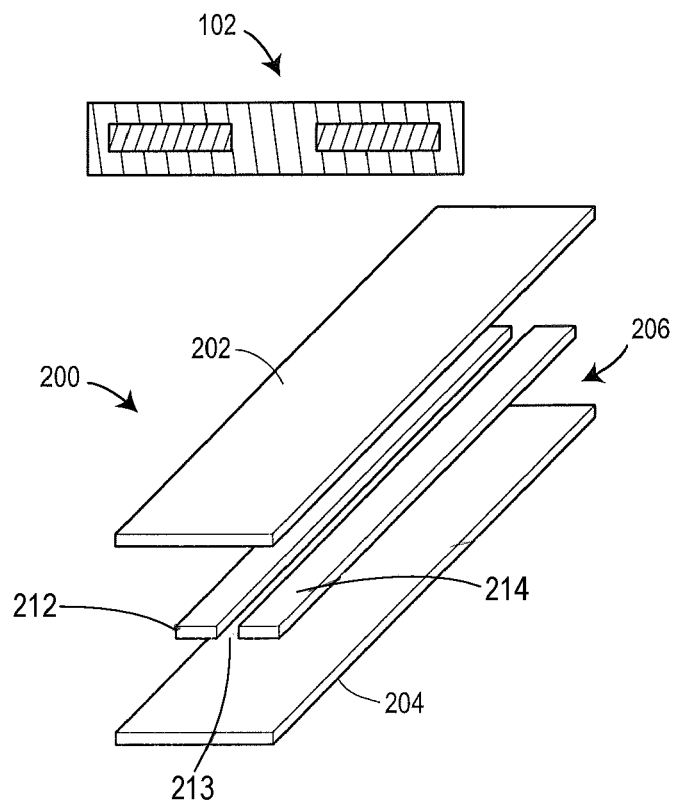
FIGS. 2A and 2B illustrate an example implementation of a wearable sensor device as may be used in the apparatus of FIG. 1, in accordance with an example.
Figure 2B:
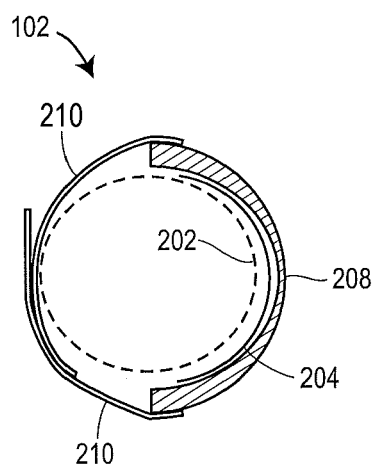
Figure 2C:
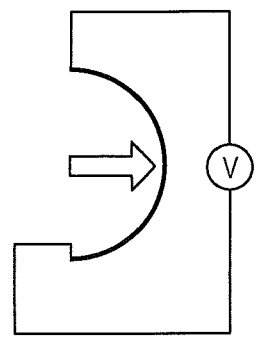
FIG. 2C is a circuit level illustration of the piezoelectric operation of the wearable sensor device of FIGS. 2A and 2B, in accordance with an example.

As illustrated in FIGS. 2A and 2B, wearable sensor 102 includes a thin piezoelectric sensor (or sensor assembly) 200 that is capable of measuring raw signal data that alters in response to blood pressure changes in a subject. The wearable sensor 102 is an example implementation of the wearable sensor 816. In some examples, the sensor 200 is triggered manually, or in other examples a controller triggers the sensor automatically. Implemented in a wearable device, the sensor may be triggered, in some examples, by a device user accessing software on a sensor controller, for example, through a touchscreen or other input device. In some examples, the sensor 200 may be a continuous sensor that collects raw signal data continually and accurately, irrespective of changes in the subject's physiological state, position, etc.

In the illustrated example, the wearable device 102 is adapted to be placed around a subject's finger, as shown in FIG. 2B. The piezoelectric sensor 200 is a multilayer structure formed of a first compliant polymer layer 202, a second compliant polymer layer 204, and an electrode layer 206 therebetween. The polymer layers 202 and 204 provide a contact surface for the sensor 200 to measure raw data correlative to changes in blood pressure. In FIG. 2B, for example, the layer 202 is proximal to a subject's finger and provides a sensing surface, while the layer 204 is disposed distally and adjacent a reference substrate 208, in the form hard backing curved substrate designed to extend at least partial around the subject's finger. The hard backing substrate 208 may be held in place by a strap 210 (such as Velcro, constant tension spring, small inflatable cuff, glove, or other adjustable band) or other suitable restraint, for example. The hard backing substrate 208 provides stability to maintain the sensor 200 in place during continual measurements and also provides a reference plane from which the highly sensitive raw data signal monitoring of the sensing surface of layer 202 can be achieved.

The electrode layer 206 may include one or more piezoelectric sensors. In the illustrated example, the electrode layer 206 includes two piezoelectric electrodes (212 and 214) that extend along a portion of or the entire longitudinal length of the sensor 200 providing a pressure sensing region that extends along a length of the subject's finger. The electrodes 212 and 214 are spaced apart by sufficiently small distance 213 to facilitate highly sensitive raw data measurements under a force applied to the sensing layer 202, and resulting in a measurable change in a sensed voltage as shown in the circuit level depiction of FIG. 2C.

The sensor 200 is able to measure a force from a subject's finger, e.g., in the form of a pressure. The applied force, which is isolatable from other potential forces affecting the subject's finger, is due to blood pressure and/or blood flow changes in the subject, which are measured as the highly accurate raw signal data. Each piezoelectric electrode 212 and 214 may function as a separate sensor, while the combination of the two (or more) can provide more accurate results as output values are combined and signal processed. Additional numbers of sensors may be used, for example, formed of parallel and co-extensive strips of piezoelectric electrodes sandwiched between the layers 202 and 204. In other examples, the piezoelectric sensors may be of different lengths to one another, or at least not all the same length. Moreover, in some examples, the electrodes are not parallel. For example, the electrodes herein may form a crossing pattern or a mesh pattern. The electrodes, for example, may be in crossing array configuration, which would have the benefit of offering mapping of the resulting blood pressure data from the sensor.

The electrodes may be formed of any suitable known piezoelectric materials, such as Gold (Au), Indium Tin Oxide (ITO). Other example known piezoelectric materials include quartz, aluminium nitride, apatite, barium titanate, lithium tantalate, lead zirconate titanate, lead scandium tantalate, lanthanum gallium silicate, bimorph, unimorph, gallium phosphate, polyvinylidene fluoride, and potassium sodium tartrate. The electrodes may be plate-like structures, as such, or wire-based structures.

In some examples, the electrodes are individually formed and placed between the polymer layers.

In some examples, the electrodes are patterned formed directly on a polymer layer. The polymer layers may be formed of a polyvinylidene fluoride (PVDF), for example. In some examples, the electrodes are embedded in a single layer. For example, two or more longitudinally extending electrodes may be formed in a PVDF layer sandwiched between layers 202 and 204, examples of which are described further below in relation to FIGS. 16 and 17.

The piezoelectric sensor 200 was tested at sensitivity levels (measured in $\mu V/Pa$) between $10\, \mu V/Pa$ to $100\, \mu V/Pa$, in some examples. These sensitivity levels are orders of magnitude better than those reported for capacitive, microfluidics based sensors and conventional piezoelectric devices. In some examples, sensor position may be calibrated based on position and/or structure. In some examples, pressure, bending, or torsion measurements may be made by corresponding sensor techniques to further this calibration.

In any event, while two piezoelectric electrodes are shown, one strip may be used or additional strips may be used, for example to improve sensor response and improve signal reliability in the presence of motion or positioning uncertainty of the subject. Each surface of the piezoelectric electrodes 212 and 214 may be formed of a thin piezoelectric polymer (PVDF) coated with a metal electrode material, examples of which are described further below.

The two polymer layers 202 and 204 may be formed of the same material and exhibit the same compression and tensile strength profiles. In this way, both layers may operate similarly under plastic deformation from the applied force at the layer 202. However, in other examples, the polymer layers 202 and 204 could be formed of different polymer materials or different thicknesses, etc. to create a relative difference in compression and/or tensile strength profiles between the layers 202 and 204. In this way, the piezoelectric sensor 200 and other sensors herein may be designed to achieve a desired level of accuracy in raw data and with an ability to amplify or de-amplify force measures obtained at the sensing layer 202.

In some examples, the sensor 200 (as well as other example sensors herein) is capable of continuous blood pressure waveform or vascular tone measurement, due to the implementation of piezoelectric electrodes 212 and 214, to produce a time history of blood pressure of a subject. While the sensor 200 is shown applied to a subject's finger, the sensor 200, and the wearable device 102, more broadly, may be applied to other areas of a subject such as the wrist, head, ankle, waist, arm, leg, neck, chest, waist, etc. For example, when used on the wrist, the sensor 200 may be entirely secured within an adjustable band, that extends around the entire wrist. An example implementation would be a wearable health monitoring device. The wearable health-monitoring device may be a device, such as a wireless-enabled bracelet type activity tracker, specially configured for gathering highly accurate and health-related raw signal data via the piezoelectric electrodes 212 and 214. Alternatively, the sensor 200, including the piezoelectric electrodes 212 and 214, may be integrated in a wearable computing or communication device, such as a smartwatch or other watch or wristband configurable to be connected (e.g., via Bluetooth) to a smartphone, tablet computer, laptop computer, etc. In such cases, the signal processing functionality of the signal processing computer 802 may be integrated into the wearable computing or communication device or may be divided between the wearable computing or communication device and another wirelessly connected computing device. In another example, when used on the head of a patient, the sensor, including the piezoelectric electrodes 212 and 214, may be integrated into a head-mounted wearable computer (e.g., a wearable computer configured to be operated in a smartphone-like hands-free manner), where the piezoelectric electrodes 212 and 214 are located adjacent to a temple of a patient.

Further, the sensor 200 may be integrated in a non-wearable computing or communication device, in an implementation. For example, the highly accurate raw signal gathering capabilities of the sensor 200 (e.g., via the piezoelectric electrodes 212 and 214) may be integrated with a smartphone, tablet computer, laptop computer, etc. In such a case, the sensor 200 may be disposed along an edge or surface of the non-wearable computing or communication device such that a patient may selectively place portions of their body (e.g., finger, wrist, etc.) proximate to the integrated sensor 200 for raw signal data retrieval via the sensor 200. In yet other examples, the sensor 200 may be integrated with these devices through a connected peripheral sensing device.

In other examples, the wearable device 102 may be implemented as a sandwiched polymer/piezoelectric structure that is adhesively mounted to a subject, such as at a subject's temple, periauricular area, nasal bridge, or other region when raw data correlative of blood pressure/blood flow may be accurately monitored.

For any of these implementations, small deformations of the piezoelectric layer 206 induced by pressure from the underlying blood vessel produces a differential voltage output.

Figure 3A:
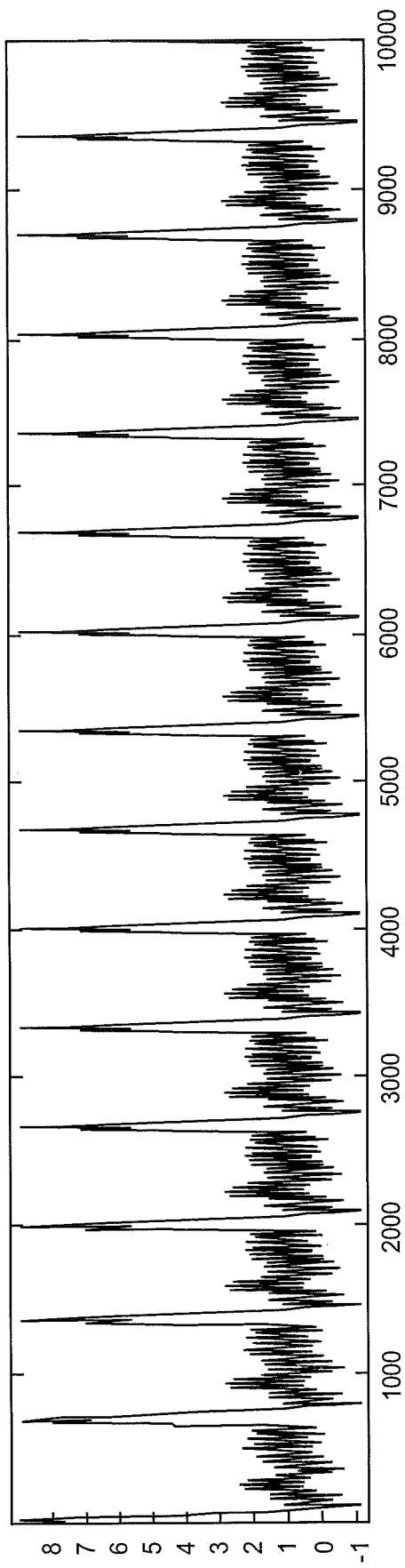
Figure 3B:
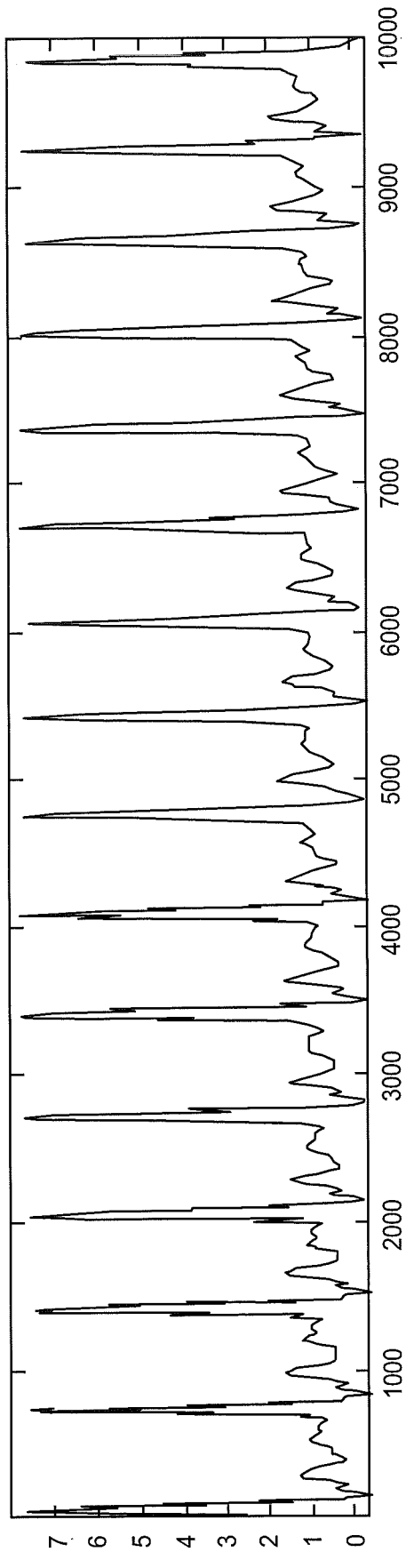
FIG. 3B illustrates a plot of the same raw signal data after initial filtering, in accordance with an example.

In operation, pressure on the sensing layer 202 produces a combination of compressive and bending deformation. The piezoelectric effect within the material, i.e., layer 206, causes an electric displacement across the thickness of the piezoelectric layer that is proportional to a combination of the axial and radial strains in the material. As shown in FIGS. 3A and 3B, the piezoelectric sensor 200 is able to produce a continual detailed record of pressure over time, where the raw data collected by the sensor 200 may be measured electronic recording instruments, such as an oscilloscope or other device as the signal-processing device 802. FIG. 3A illustrates the raw signal data the wearable device 102 communications to the signal-processing device 802, and as may be displayed prior to any signal filtering. FIG. 3B illustrates the raw signal data after an initial filtering by the signal-processing device 802.

The piezoelectric sensors described herein may be capable of providing a passive transduction mechanism, small in size, with high sensitivity, and flexible use. The sensors offer substantial advantages over existing blood pressure measuring systems, in this way. Moreover, the piezoelectric electrodes require no external power supply, while the resulting raw signal data exhibits high signal-to-noise ratio, even without external amplification of the signal.

To facilitate measurement, in addition to piezoelectric electrode spacing, the electrodes 212 and 214 can be on the order of just a few millimeters in cross-sectional thickness, allowing for non-invasive use that is much less cumbersome than existing blood pressure monitors. The use of a very thin piezoelectric layer 206 results in high sensitivity to blood pressure, while allowing flexibility to shape the sensor around fingers and wrists of varying size.

Figure 4:
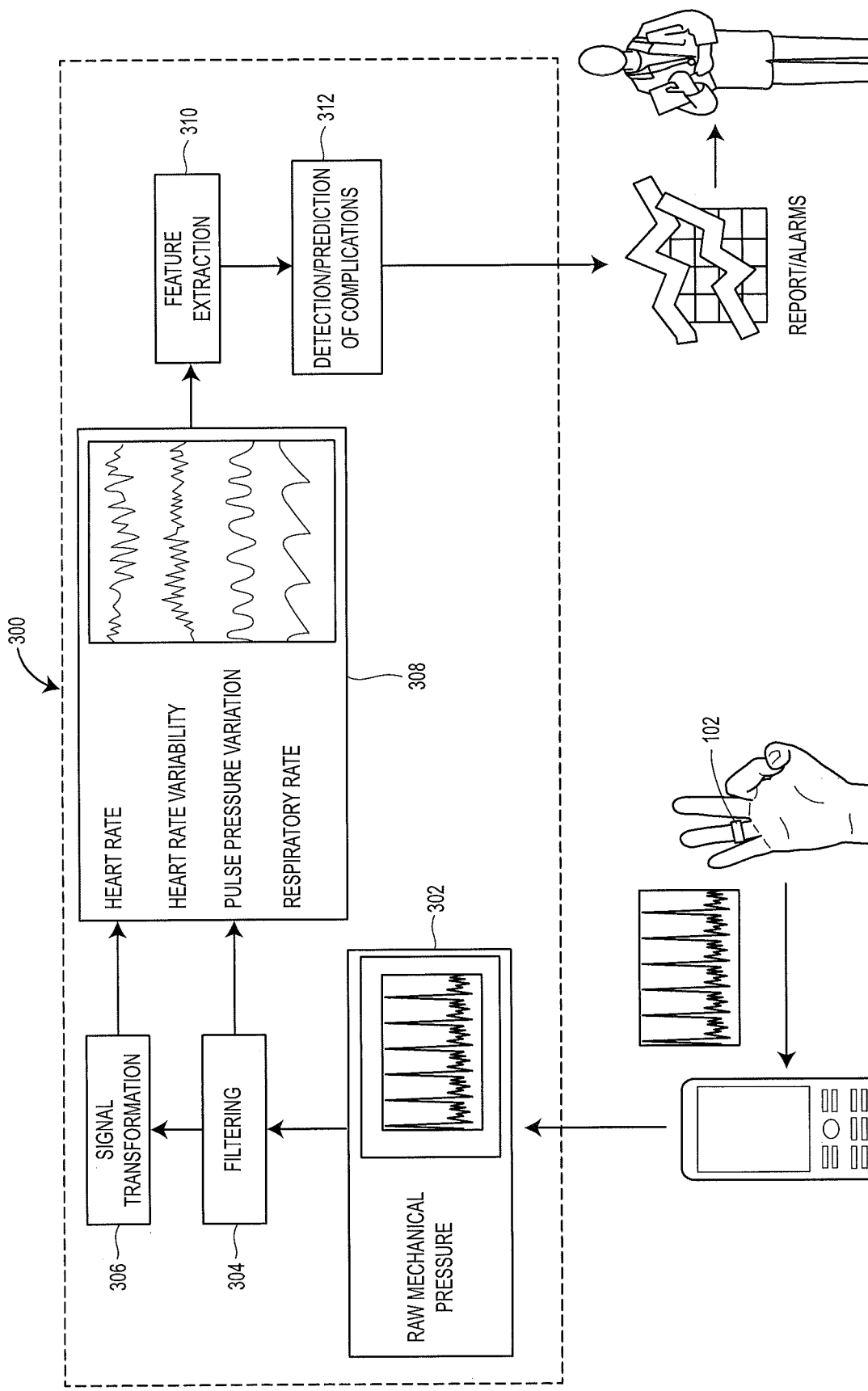
FIG. 4 is a schematic diagram of a signal processor implemented in the apparatus of FIG. 1 to extract the physiological conditions, in accordance with an example, in accordance with an example.

FIG. 4 illustrates a signal processing system 300 capable of extracting one or more physiological conditions from the raw signal data of the wearable device 102. The system 300 is discussed in reference to example processes 400 and 500 in FIGS. 5 and 6, respectively. The processes 400 and 500 differ in the type of sensor inputs that may be applied and therefore in the number of waveform features that may be extracted from the raw signal data. But otherwise the processes 400 and 500 are similar; and therefore, like reference numerals are used.

Figure 5:
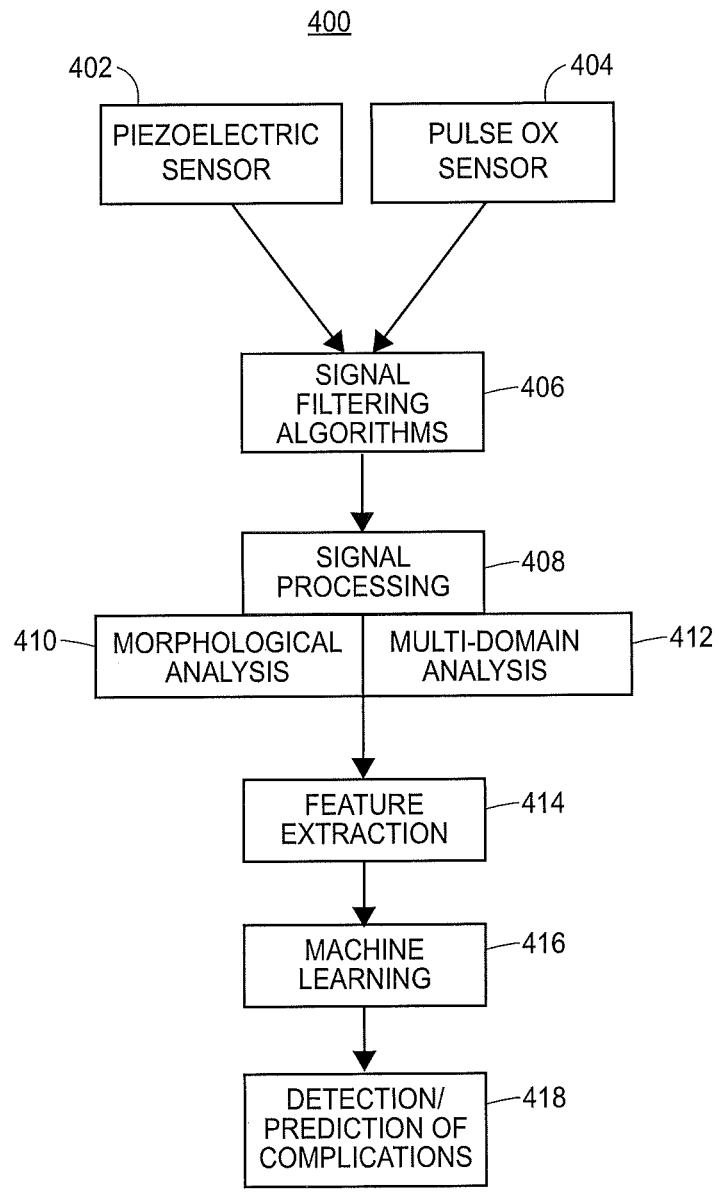
FIG. 5 is a flow diagram of operation of signal processor of FIG. 4, in accordance with an example implementation of FIG. 1, in accordance with an example.

In reference to FIG. 5, at blocks 402 and 404 raw signal data from piezoelectric sensor 200 and a raw signal data from secondary sensor are provided to the signal processor system 300, for example through a wireless or wired interface. An example two sensor device, in the form of a piezoelectric sensor and pulse-oximetry sensor, is described further with reference to FIGS. 14A, 14B, and 14C, as well as FIGS. 16, 17, and 18. Wired interfaces may include twisted pair, coaxial, ribbon, fiber optic, etc. cable facilitating communications via any suitable wired networking protocol, such as a protocol as standardized in IEEE 802.3. Wireless interfaces may include one or more wireless routers, modems, antennas, transceivers, etc., facilitating communications via any suitable wireless networking protocol, such as Bluetooth or a protocol standardized under IEEE 802.11. In some implementations, communications between the sensor 200 and the signal processor system 300 may follow a proprietary protocol or protocol specially configured for health-related or activity-tracking applications. The raw signal data is collected at a raw mechanical pressure converter 302, which provides the raw signal to a filtering stage 304 that applies signal filtering algorithms 406 of FIG. 5. In this way, the block 402 provides raw signal data, in real time, where that raw signal data is a blood flow dependent data measurement. The block 404 provides signal data from a secondary sensor, e.g., one collecting photoplethysmograph derived blood flow and hemoglobin oxygen saturation data, through the use of a radiative reflectance or radiative transmission signal.

Via a block 408, a transformation stage 306 performs a signal decomposition on the filtered, received raw signal data. Because of the high sensitivity of the wearable sensor 102 and the piezoelectric sensor 200, in particular, raw pressure signal inherently contains a multitude of vital information regarding a subject's physiological state. This decomposed signal data from the stage 306 and the filtered raw data from the stage 304 are provided to feature extraction analysis stage 308. The stage 308 contains algorithms for extracting any of a plurality of different waveform features from the received raw signal data. For example, the stage 308 may be designed to analyze raw signal data and extract any number of features from the waveform and thereby identify any number of physiological conditions expressive by one or more of the waveform features, including, but not limited to blood pressure (BP), pulse pressure (PP), pulse pressure variability (PPV), heart rate (HR), heart rate variability (HRV), arterial wall stiffness (AWS) or other vascular wall motion related features, blood flow (BF), and respiratory rate (RR). In various examples discussed below, feature extraction from pressure sensor and pulse-oximetry sensor data may include applied power from a peripheral member such as from a subject's finger, vascular radius, and vascular resistance/vascular stiffness.

To achieve feature extraction, the stage 308 may perform morphological analyses at a block 410 and multi-domain analyses at a block 412 to extract features that are provided (from both blocks) to a feature extraction module 310, via block 414. The stage 308 may access historical blood pressure or blood flow data or other previously-collected data correlative to physiological features such as blood pressure (BP), pulse pressure (PP), heart rate (HR), heart rate variability (HRV), arterial wall stiffness (AWS), blood flow (BF), pulse transit time (PTT), Cardiac-vascular power (CVP), or respiratory rate (RR). That historical data may include data collected from different subjects, collected solely from the subject under examination, collected from a subset of subjects having common physiological features with the subject, or some combination thereof. Such data may be analyzed, at least in part, through morphological analysis block 410.

In performing the domain analysis of block 412, the stage 308 may perform raw signal data extractions by identifying one or more signal (waveform) features in the data. These signal features may include identifying global and local peaks and troughs within the raw signal data, as well as spacing distances (or periods) between features. FIG. 7A illustrates a segment of raw signal data before artifact removal. FIG. 7B illustrates the same segment, after artifact removal and after the stage 308 has performed raw signal data extractions, where at least some of the spacing distances (or periods) between features may be related to vascular wall reflections from the more proximal vasculature (portions of the aorta). These peaks, while arbitrarily labeled in FIG. 7B may vary in peak, width, and spacing to each other based on important changes in physiology and treatment.

The output voltage from the wearable device 102 may be linearly dependent on pressure, but the linear coefficient may vary based on "ring location" of the wearable sensor on the finger, position of the finger, and tightness of fit. As such, in some examples, physiological details are taken from the relative height of waveform features in the raw data signal and variation in the signal over time, as opposed to exclusively by absolute voltage output. What we've found, remarkably, is that the actual mechanical properties of the movement of the arterial wall can be measured producing incredible waveform information similar (and for some features enhanced) to that produced by an indwelling catheter in the artery measuring pressure changes.

In any event, the particular features to be extracted by the stage 308 may be selected as those that are considered important pre-cursors in the monitoring of a subject's physiological condition. The selected extracted features, therefore, may provide valuable insights into the abnormalities of the morphology of the pressure signal to help identify disease cases. In some examples, the extraction data from block 414 may be provided to a block 416, also implemented in stage 310, where machine learning may be performed to optimize feature extraction and data analysis. Example machine learning implementations include decision tree learning algorithms, clustering algorithms, support vector machine algorithms, pattern recognition algorithms, feature selection algorithms, and others known to those skilled in the art.

In particular, signal processors may optimize and/or detect time-based waveform features in raw signal data via machine learning techniques. A signal processor may detect all peaks in a raw signal using a hierarchical method that applies a derivative of the original signal to the raw signal. The timing between all peaks as well as the relative amplitudes of the peaks within the same pulse may be calculated. The signal processor may aggregate and use these values as features directly calculated from time signal.

Further, signal processors may utilize transform-based techniques to optimize and/or detect features in raw signal data. A signal processor may transform a windowed portion of the raw signal data into other domains using transforms, such as Stockwell transforms (S-transform) and/or Dual Tree Complex Wavelet Transforms (DTCWT). Then, for any given window, the signal processor may extract multiple features in each domain. For instance, entropy of DTCWT coefficients or the statistical averages on the max frequencies across the window may be extracted. It is clear however that any suitable features and number of features may be extracted in each domain.

Signal processors may also utilize machine learning, based on extracted features, to predict physiological events/complications. Feature, such as those discussed above, or subset of features may be input to a machine learning algorithm, which is trained to predict one or more targeted physiologic events, such as hemorrhagic shock. By example and without limitation, such a machine learning algorithm may utilize SVM, Random Forest, Neural Networks, ECOC combined with SVM, and ensemble classifiers to predict the one or more targeted physiologic events.

In some examples, the system 300 takes the extracted data from stage 310 and performs morphology detection and/or prediction a subject using a stage 312 and at a block 418. The output data from the stage 312 may be displayed as a health report and/or alarm condition, for example, using the display 826 of signal-processing device 802, a health report and/or alarm condition may be displayed as a web page, mobile alert, tactile alert or alarm (e.g., via a vibrating function of a smartwatch or smartphone), or any other suitable visual and/or tactile display. While in other examples, the output data is provided to a treatment system, such as therapeutic delivery system for administering a therapeutic treatment to a subject. That delivery system may include an administration system having therapeutic delivery vehicle in communication with a therapeutic treatment processor that controls delivery of the therapeutic treatment in response to received patient status data. In this way the system 300 may be part of a closed loop system with a treatment system, where the latter is design to administer a therapeutic treatment in response to the stored one or more extracted features from the former.

Figure 8:
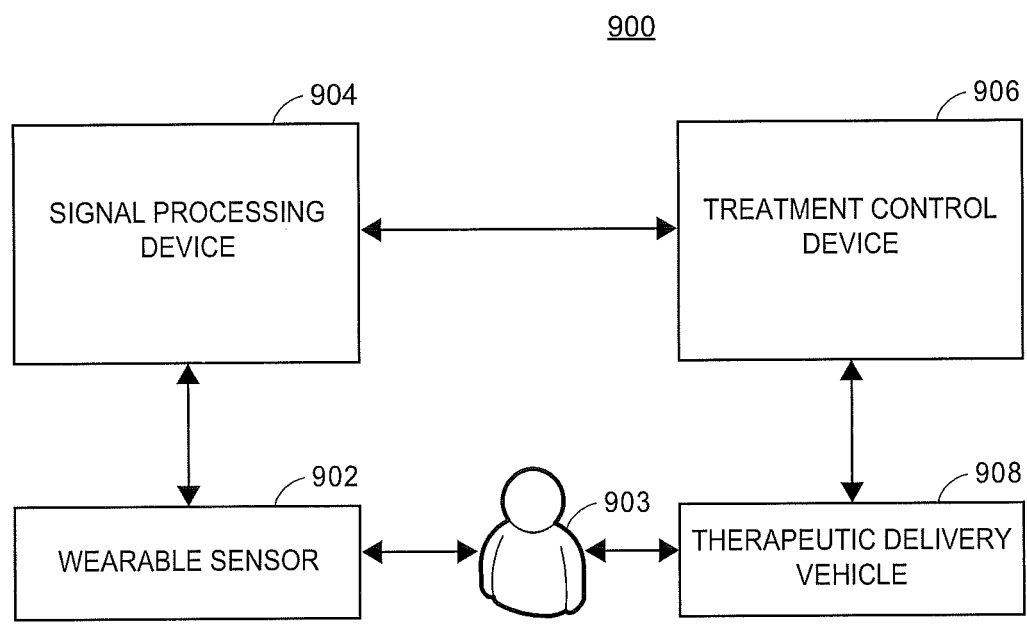
FIG. 8 is a schematic of a therapeutic delivery system for administering a therapeutic treatment to a subject using the apparatus of FIG. 1 in a closed loop manner, in accordance with an example.

FIG. 8 illustrates an example closed loop system 900 in which a therapeutic treatment may be administered in response to a stored one or more extracted features. A wearable sensor assembly 902, in accordance with the teachings herein, is attached to a subject 903. The sensor assembly 902 measures blood pressure through a piezoelectric sensor within the assembly 902. In dual (or multiple) sensor devices, the assembly 902 further measures blood flow using a secondary sensor of the assembly 902. In some examples the wearable sensor assembly 902 includes plurality of sensors, including one or more of a temperature sensor, a motion sensor, an actigraphy sensor, a galvanic skin response sensor, an impedance sensor, or any combination thereof.

A signal-processing device 904, having one or more processors and one or more memories, is coupled to the assembly 902 to perform such operations as receiving raw signal data, filtering the received raw signal data, perform signal decomposition on the filtered raw signal data, extracting one or more features of the sensing region, and analyzing blood flow data, and extract feature indicators of circulating vascular volume and vascular tone. These features include, as described in examples below, vascular resistance, vascular stiffness, vascular radius, and/or applied power.

The signal-processing device 904 is configured to automatically analyze the wearable sensor data and compare that data to recently-recorded or historically-recorded data to allow for more accurate analysis of the signal data. The signal-processing device 904 may determine, from the analyzed data, characteristics such as subject (903) stress level, presence of hypertension, a syncope or hypotension susceptibility and warning, the presence of Raynauds disease, the presence of potential sickle cell disease, sepsis, shock, sleep apnea, respiratory state (asthma, COPD exacerbations) and even whether a patient has had a cardiac arrest and other conditions expressed by blood flow levels and/or changes thereto.

The signal-processing device 904 is coupled to a treatment control device 906 that determines a treatment regimen based on the received processed data. The treatment control device 906 may be an existing treatment device, such as an infusion pump, that controls a therapeutic delivery vehicle 908 capable of delivering a blood pressure medication (vasopressors such as norepinephrine or vasodilators such as nitroprusside), sedation agents, volume expanders, and others. The signal-processing device 904 could be made part of an extracorporeal circuit such as a dialysis machine that could adjust flow if the sensor and signal-processing device predicted the near occurrence of a drop in blood pressure. Similar strategies could be developed for other treatment control devices like mechanical ventilators that allow adjustment of ventilation parameters based on their effects on the sensor data. For example, the signal-processing device 904 may be configured to identify local peaks in the received data from the sensor (including peak data for each different sensor type within the sensor) and from a difference in peak values determine a vascular volume and/or vascular tone.

The process 400 may include performing feature extraction (414), the optional machine learning (416), and/or the optional morphology detection/prediction (418), using demographic and related health information of the user, where available. Either way, the machine learning algorithm of block 416 may assess the extracted features, predict the progression and occurrences of critical states and in conjunction with the block 418 provide clinical recommendations to care givers as well as to patients themselves.

Figure 6:
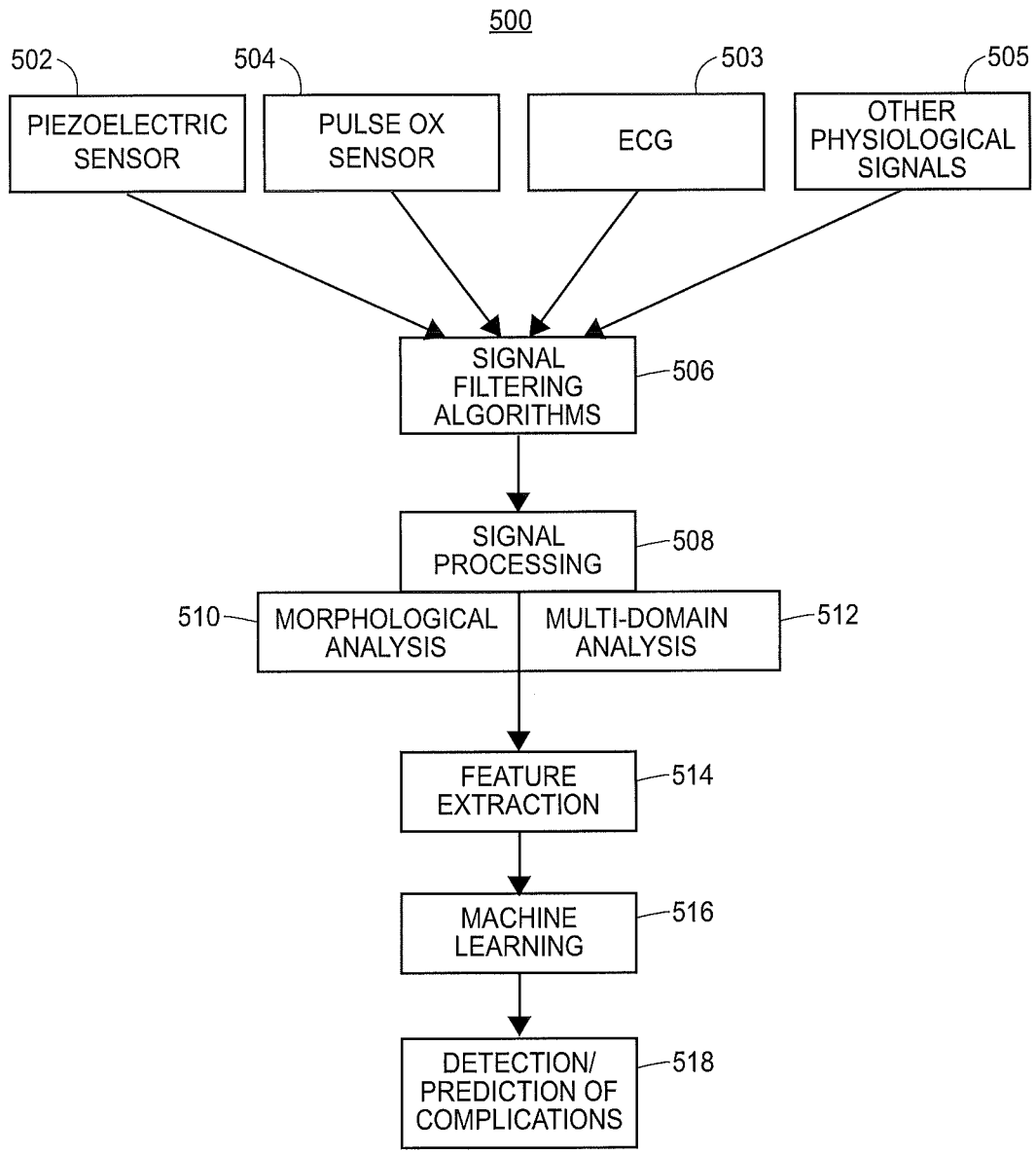
FIG. 6 is a flow diagram of operation of signal processor of FIG. 4, in accordance with another example implementation of FIG. 1, in accordance with an example.

The process 500 in FIG. 6 is similar to that of process 400 (and thus bears reference numbers 506-516 corresponding to reference numerals 406-416), except that in addition to data collected from a piezoelectric sensor 502 and a pulse-oximetry sensor 504, electrocardiogram (ECG) data is collected at a block 503 and other physiological signals may be collected at a block 505. These other physiological signals include temperature, tissue impedance, galvanic skin response, and movement, among other physiological signals.

FIGS. 9, 10, 11, and 12 illustrate an example scenario in which data is gathered from a sensor assembly with both piezoelectric and pulse-oximetry sensors. Signals from both sensors may be received from the same sensor assembly (e.g., on a finger) while a patient performs several physiologic maneuvers such as deep breathing, Valsalva, or others. Note, although FIGS. 9, 10, 11, and 12 illustrate data from both piezoelectric and pulse-oximetry sensors, additional data may be obtained from sensor assemblies with additional sensors, such as ECG, impedance, temperature and other signals.

Figure 9:
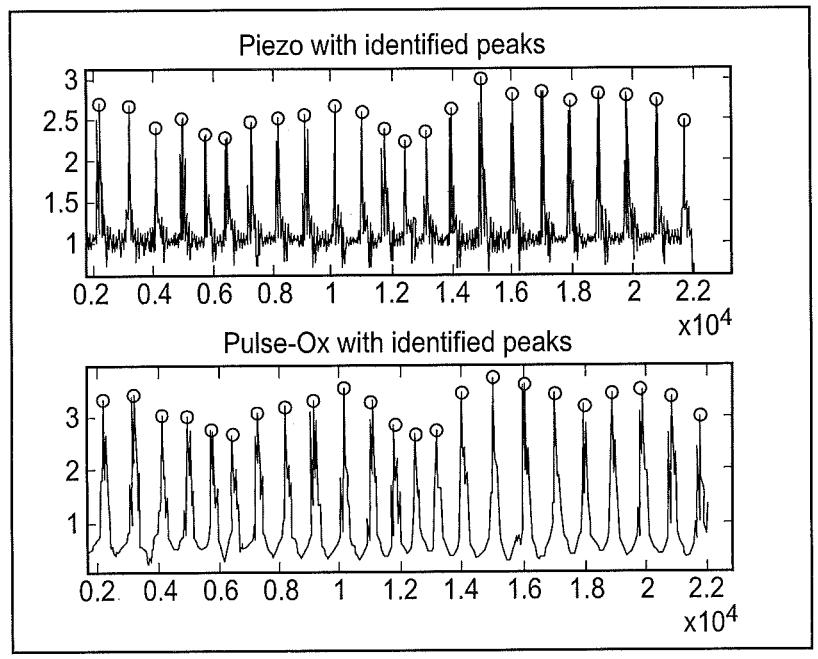
FIG. 9 illustrates an automated peak detection within a window of both piezoelectric and pulse-oximetry waveforms, in accordance with an example.

As illustrated in FIG. 9, an algorithm (e.g., executed by the signal-processing device 802) is capable of automatically detecting the peaks of each signal after denoising/filtering. FIG. 9 depicts an automated peak detection within a window of both piezoelectric and pulse-oximetry waveforms.

Figure 10:
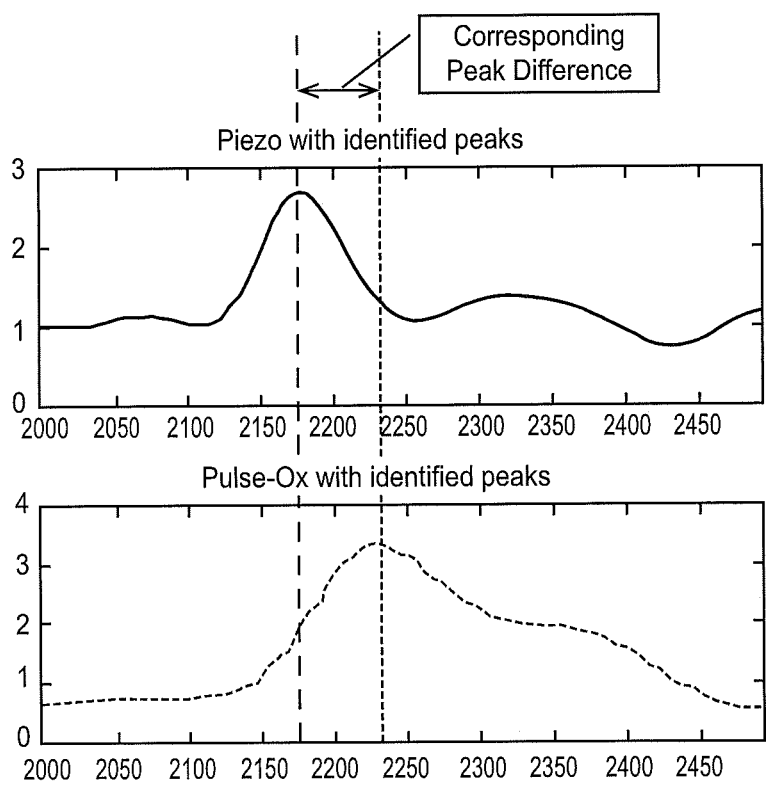
FIG. 10 illustrates example measured peak differences between corresponding peaks of the pulse-ox and piezoelectric waveforms, in accordance with an example.

Using the detected peaks, a distance in time ("x-axis") between peaks in the piezoelectric and peaks in the Pulse-ox is computed. FIG. 10 illustrates example measured peak differences between corresponding peaks of the pulse-ox and piezoelectric waveforms. In some implementations, in order to accurately measure the time difference between peaks in the two signals, a filtering and pre-processing of the two signals needs to be coordinated or conformed.

In the example scenario, both the piezoelectric and pulse-oximetry signals are collected from a patient while the subject performed some specified breathing exercises/maneuvers. The pulse-ox and the piezoelectric sensors may be disposed at a location very close to each other and on one the finger of the individual. The breathing maneuvers performed by the individual, whose data is depicted in FIGS. 9 and 10 may include, by way of example: (i) Baseline—sitting still and breathing normally; (ii) Valsava—closing one's mouth, pinching one's nose shut while pressing out as if blowing up a balloon; (iii) Deep breathing: repeated deep breaths; (iv) Fast breathing—repeated rapid brething with shallow breaths; (v) BP cuff inflation and deflation—where a BP cuff is attached to the he subject's upper arm to which the other sensors are connected, the cuff is then inflated until the pulse-oximetry signal flat-lines, and, after keeping the cuff inflated for 2 minutes, the cuff is suddenly deflated to allow the return of normal circulation.

Figure 11:
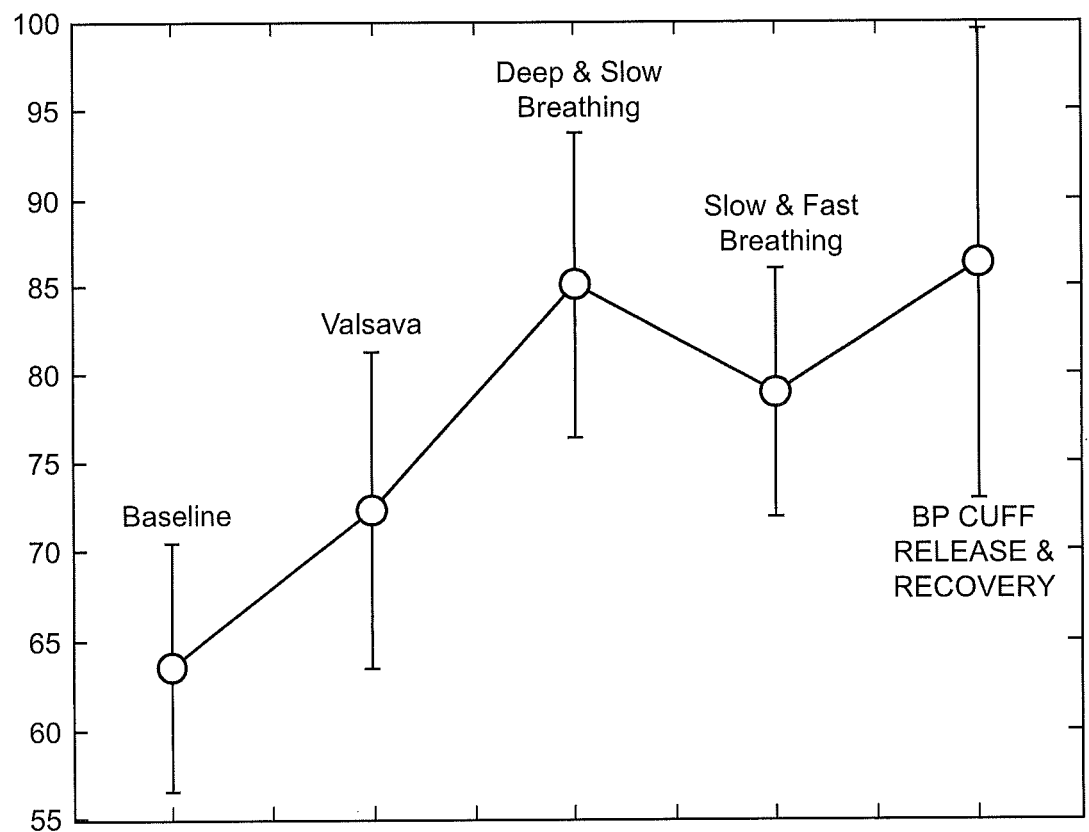
FIG. 11 depicts example means and standard deviations of different maneuvers calculated over corresponding peak differences between pulse-oximetry and piezoelectric waveforms, in accordance with an example.

FIG. 11 depicts the means and standard deviation of different maneuvers calculated over corresponding peak differences between pulse-oximetry and piezoelectric waveforms. It can clearly be seen that the peak-difference varies between baseline and other maneuvers.

Figure 12:
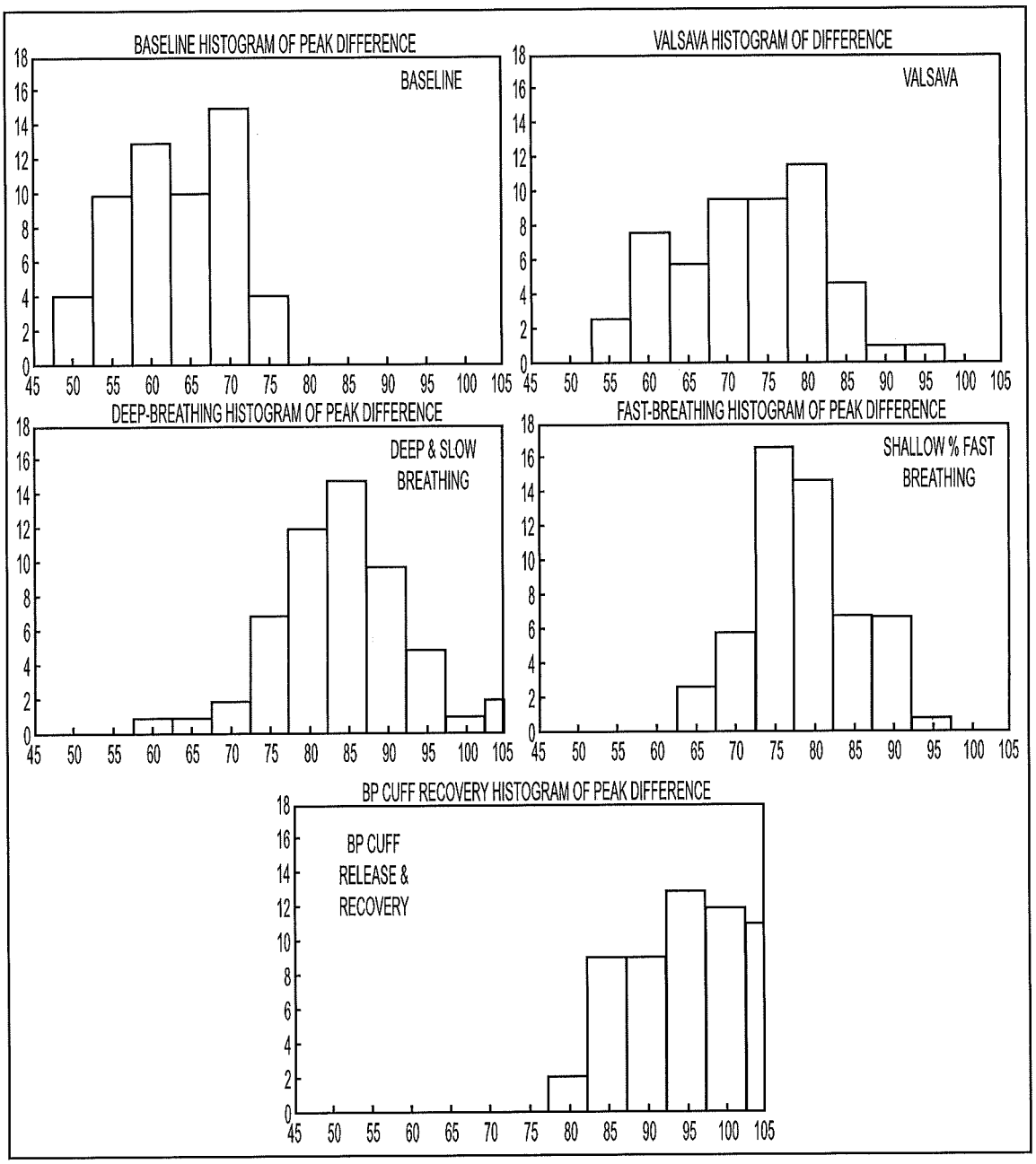
FIG. 12 includes example histograms of the peak differences between different maneuvers, in accordance with an example

FIG. 12 includes example histograms of the peak differences between different maneuvers. Using fixed window sizes, the peak differences and corresponding distributions may be computed. As clearly seen in FIG. 12, the histograms vary considerably displaying the ability of computed peak difference to distinguish between different maneuvers.

FIGS. 13A-13G illustrate plots of piezoelectric sensor raw data compared to measured data from a pulse oximeter, under different conditions of a subject.

The output of the piezoelectric sensor may be linearly dependent on pressure, but the linear coefficient may vary based on location of a sensor assembly and tightness of fit. As such, physiological details may be inferred from relative height of features in the output signal and variation in the signal over time, not by absolute voltage output.

Figure 13A:
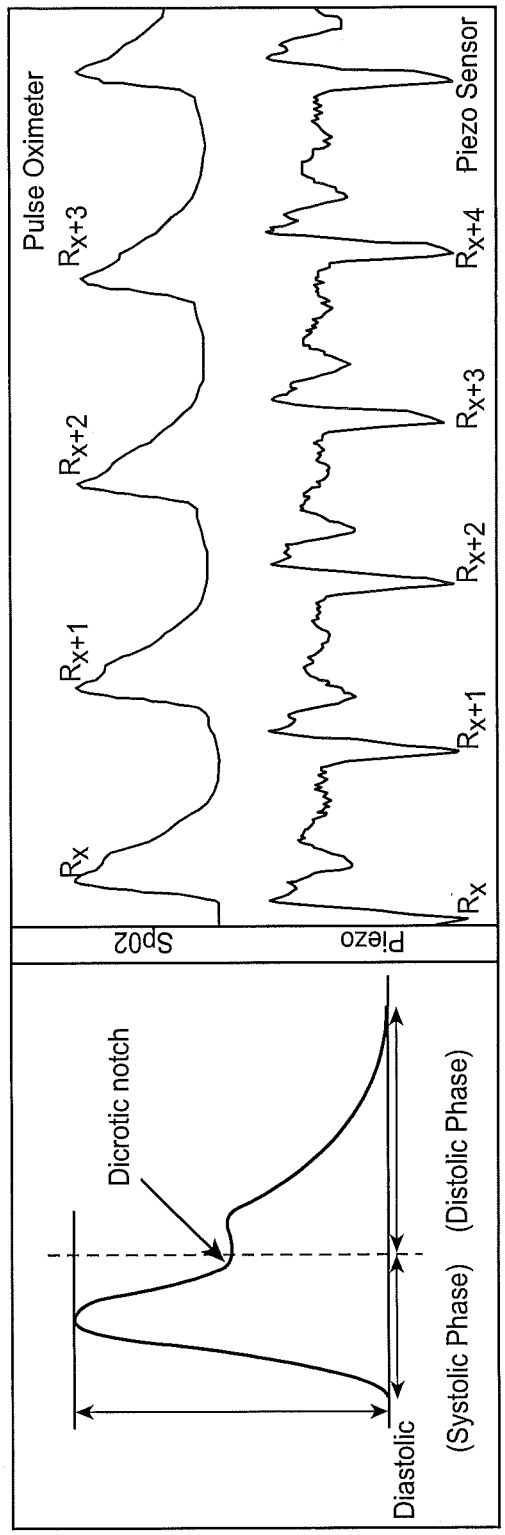
FIGS. 13A-13F illustrate plots of raw data collected from the piezoelectric sensor and used for extracting physiological conditions under different conditions of a subject, in accordance with an example.
Figure 13B:
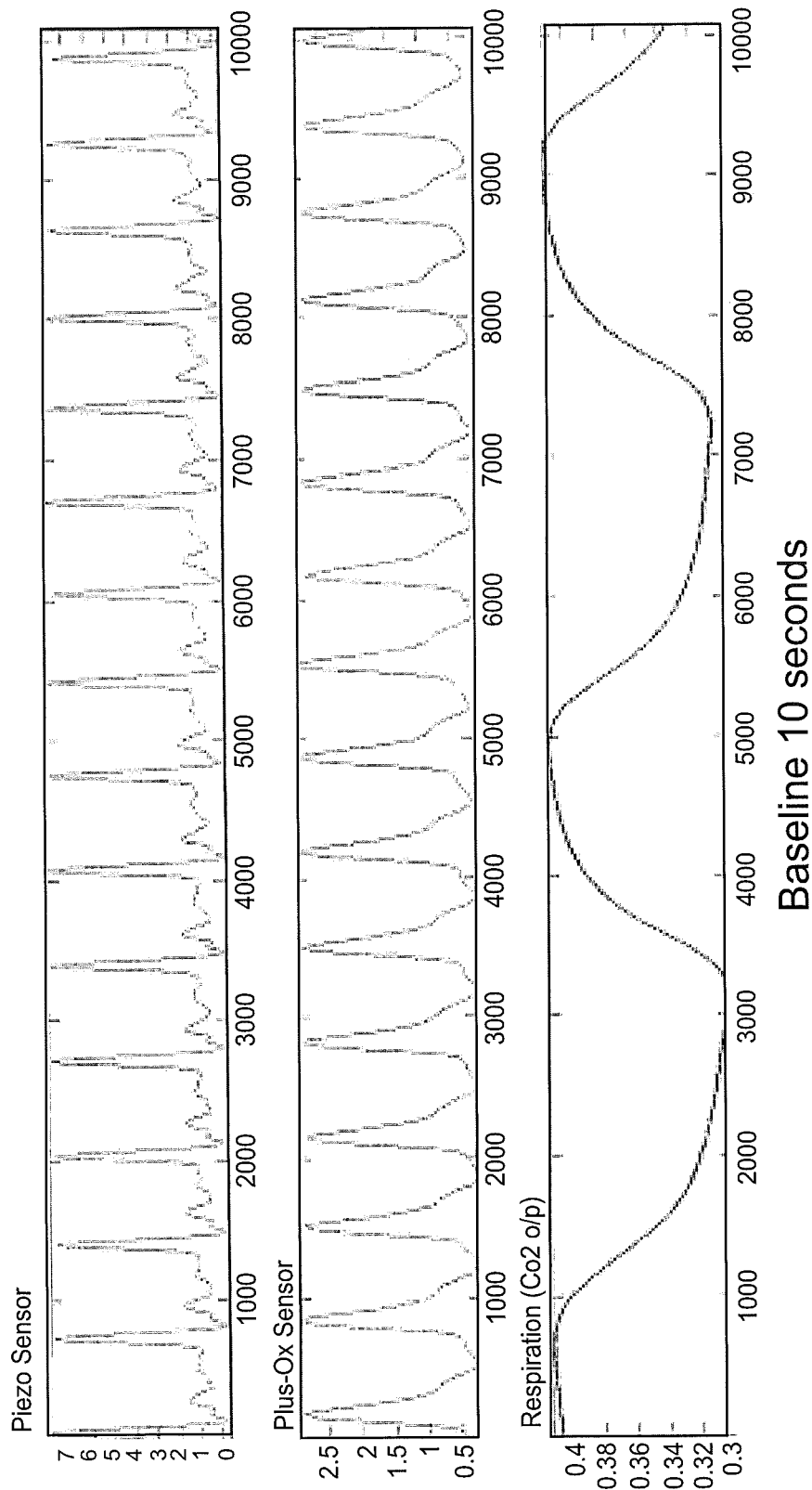
Figure 13C:
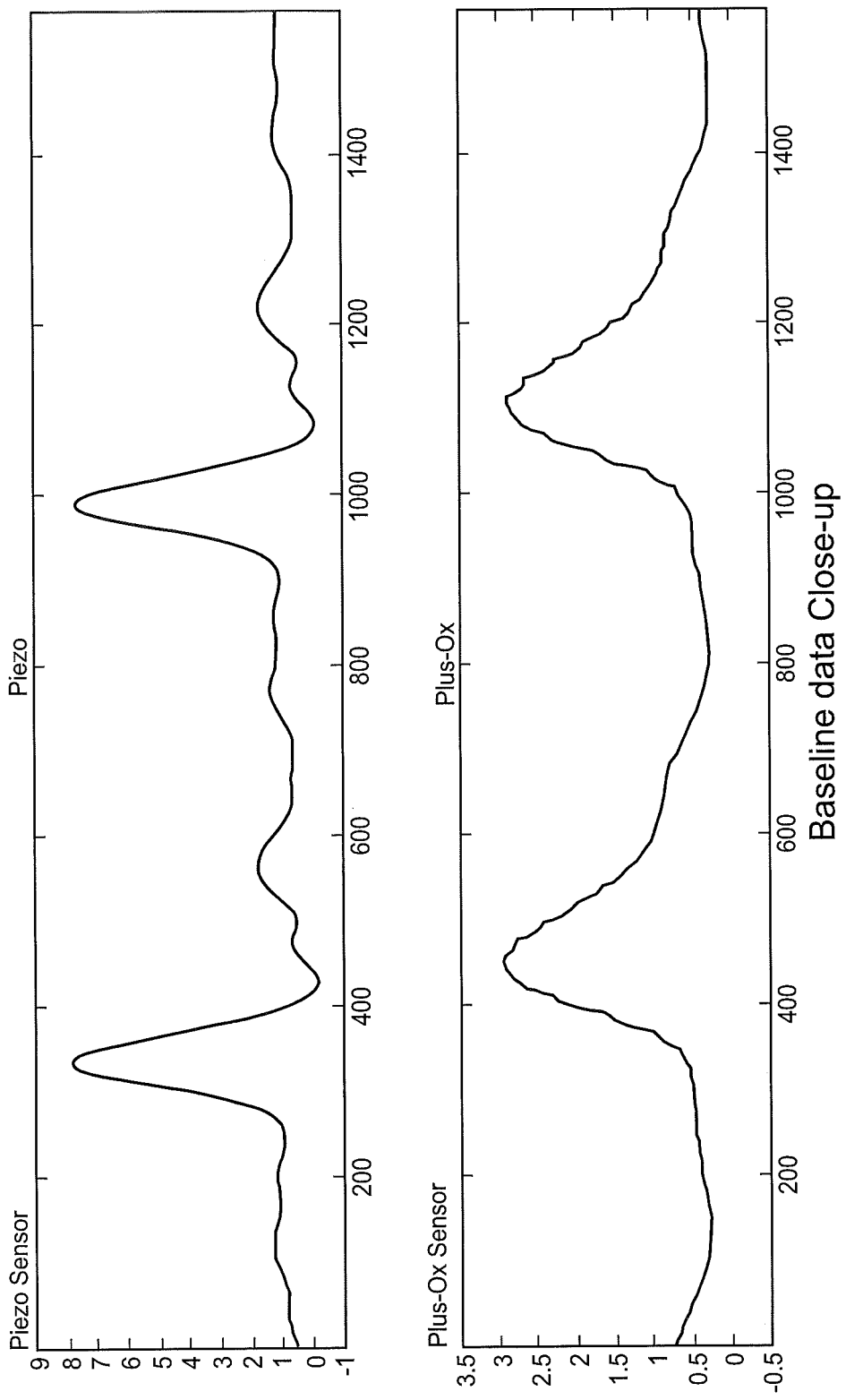
Figure 13D:
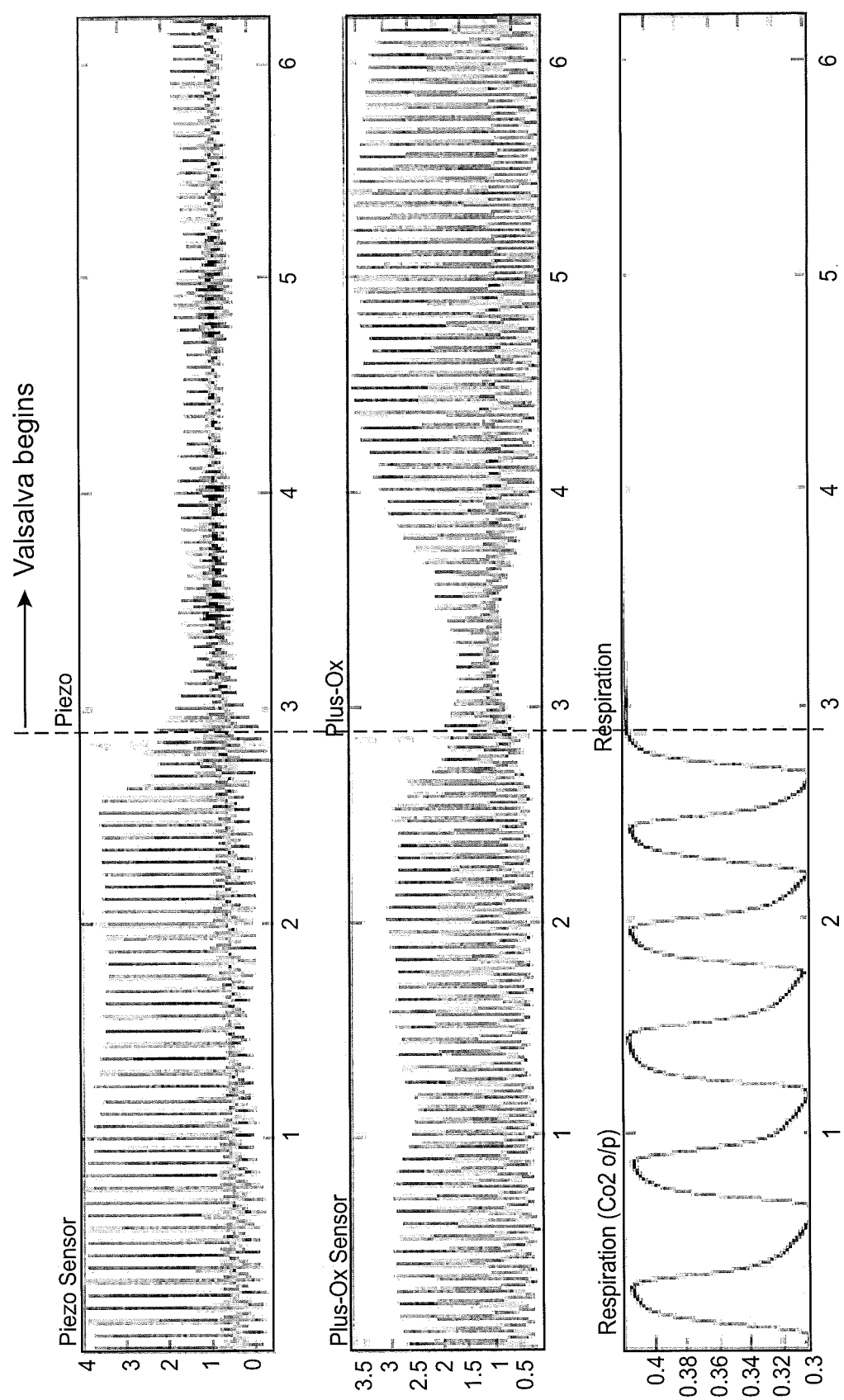
Figure 13F:
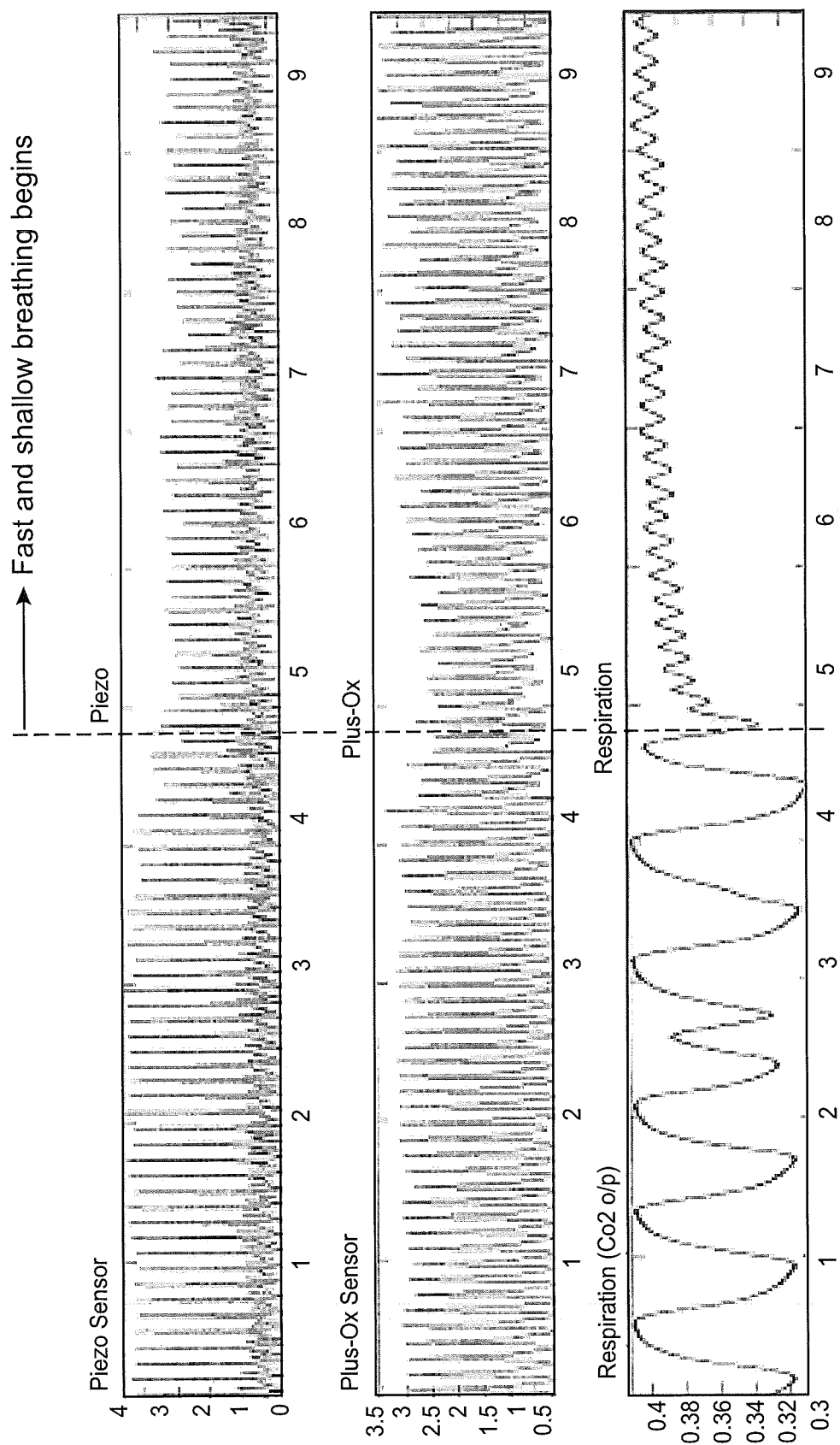
Figure 13G:
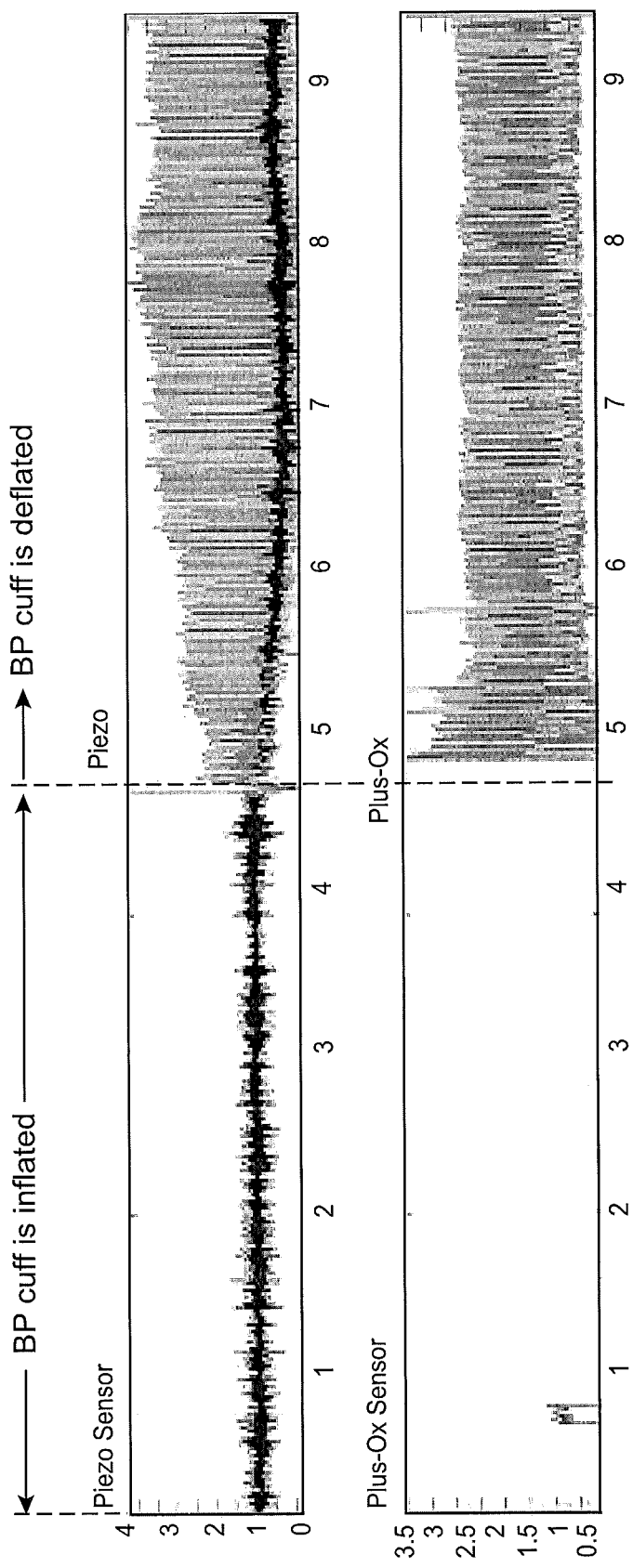

In some cases, the actual mechanical properties of the movement of the arterial wall (or vascular wall movements) may be measured producing rich waveform information similar to that produced by an indwelling catheter in the artery measuring pressure changes (see FIG. 13A) with some features actually being enhanced over traditional fluid column pressure monitoring. As shown in FIGS. 13A, 13B, and 13C, the waveform acquired from the piezoelectric sensor is very similar but also richer in features than the waveform produced by the pulse-oximetry sensor. Also, as shown in FIGS. 13D, 13E, 13F, and 13G the piezoelectric waveform may include unique trends which can be utilized to distinguish between different breathing maneuvers including Valsalva (see FIG. 13D), deep breathing (see FIG. 13E), fast breathing (see FIG. 13F), and BP cuff inflation (see FIG. 13G).

Further, high fidelity signals from piezoelectric sensors may be used, in some implementations, to reduce false alarms from traditional invasive and noninvasive monitoring methods for a number of applications. Such a use may reduce alarms caused by: (i) traditional pulse-oximetry in which the plethsymographic waveform produced is not of good fidelity due to motion or misapplication of the probe(s) or electrodes; (ii) dampening of arterial blood pressure monitoring waveforms from air bubbles and other problems caused by the nature of transducing pressures via fluid columns; and (iii) ECG alarming from the presence of electrical interference, motion induced artifacts of the ECG, or impedance respiratory signals or monitoring.

The nature of the direct mechanical high fidelity waveform, or raw signal data, produced by the piezoelectric sensor thus has the capability of acting as a signal "check" against electrical, water column transduction, and other signal acquisition methods. For example, maintenance of a clear piezoelectric waveform in the presence of a dampened invasive arterial pressure or pulse-oximetry waveform may indicate or produce a signal that would indicate that an alarm is due to faulty placement or function of sensors. Signals from the current piezoelectric sensor could also indicate that ectopy is true ectopy and not caused from motion or electrical interference, or the Signals from the current piezoelectric sensor could be used to confirm changes in respiratory rate.

Figure 14A:
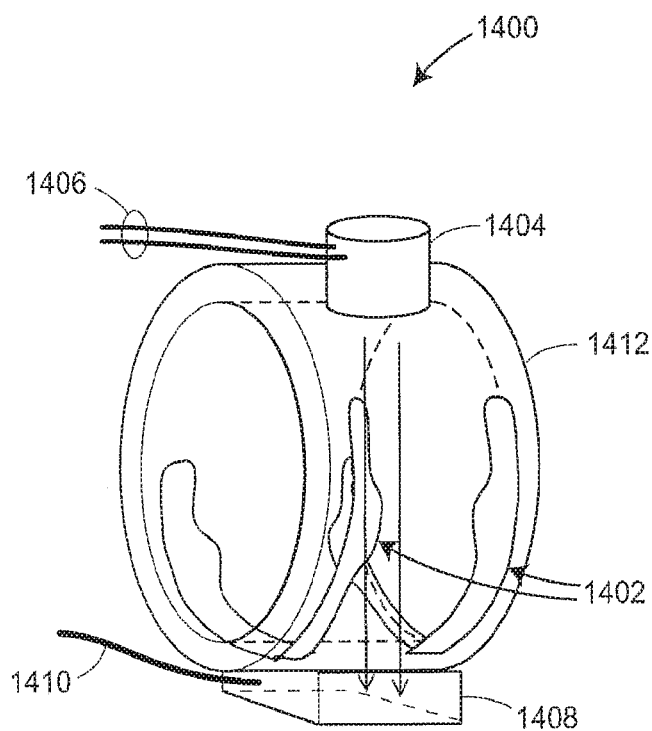
FIGS. 14A and 14B illustrate an example two sensor device, in the form of a piezoelectric sensor and pulse-oximetry sensor, in accordance with an example.
Figure 14B:
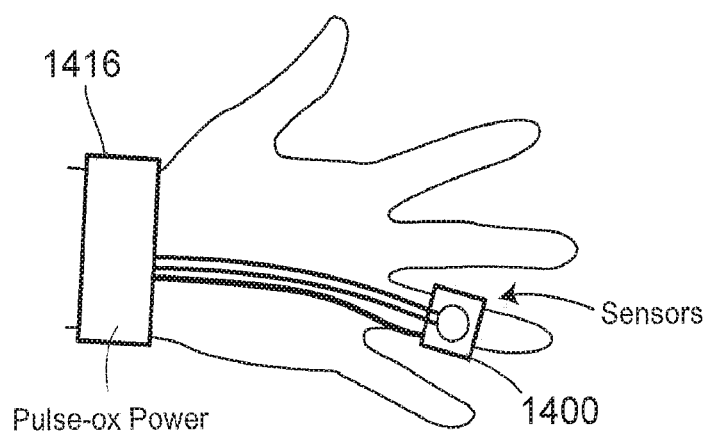
Figure 14C:
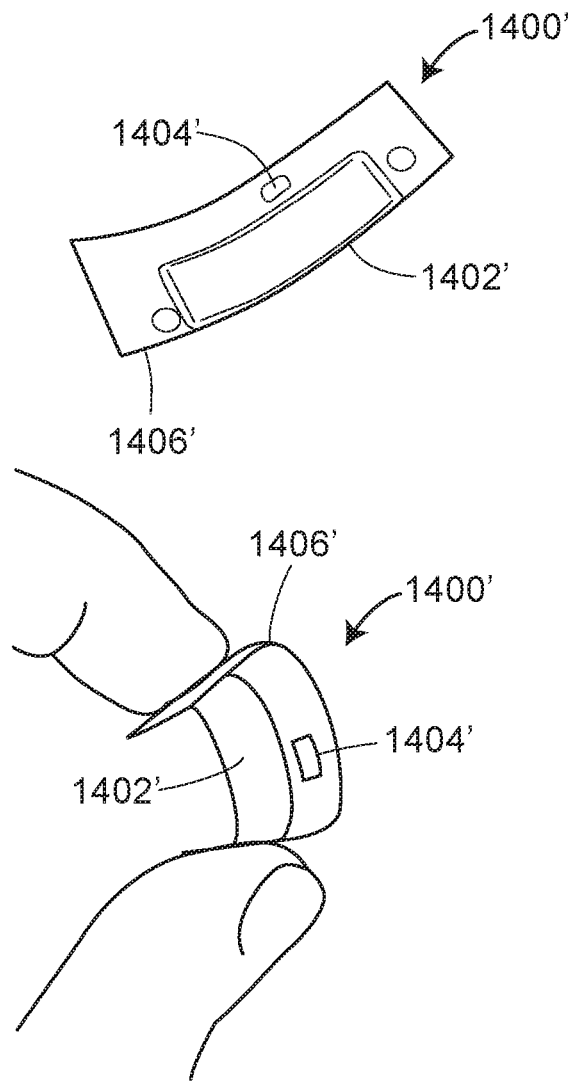
FIG. 14C illustrates an example two sensor device, having a piezoelectric sensor and pulse-oximetry sensor formed in an integrated thin film sensor, in accordance with an example.

FIGS. 14A and 14B illustrates an example two sensor device 1400, or sensor assembly. The two sensor device 1400 includes one or more piezoelectric sensors 1402 and one or more other components associated with a pulse-oximetry sensor. The example pulse-oximetry sensor components may include a light source 1404 (powered via electrical connections 1406) and a light sensor 1408 operatively connected to one or more receiver connections 1410.

A support structure component 1412, such as a structure or band constructed as a polymer laminate (including, for example, a PVDF laminate), may support the piezoelectric sensors 1402 and the pulse-oximetry sensor components 1404 and 1408 such that they are positioned to gather vascular wall motion and blood flow dependent measurements. For example, as illustrated in FIG. 14B, the two device sensor 1400 may attach to a finger of a patient (e.g., via snap closures, buttons, buckles, or other attachments as discussed above). However, generally speaking, the support structure component 1412 and integrated attachment mechanisms (not shown) may allow the two sensor device to be attached to and gather measurements from any suitable portion of a patient's body. Also, although a pulse-oximetry sensor is illustrated with respect to FIGS. 14A and 14B, the two sensor device 1400 may include the piezoelectric sensors 1402 and a temperature sensor, motion sensor, actigraphy sensor, galvanic skin response sensor, impedance sensor, or any combination thereof.

In some implementations, the piezoelectric sensors 1402 may operate as passive sensor, whereas the pulse-oximetry sensor components 1404 and 1408 may require a power source to operate. In such a case, the two sensor device 1400, or pulse-oximetry components of the two sensor device 1400, may be operatively connected to a wearable power supply 1416. For example, the wearable power supply 1416 may include any suitable portable power source, such as batteries, solar panels, etc. It is clear, however, that the power supply 1416 may be integrated into the two sensor device 1400 such that the two sensor device does not require external power connections or leads.

In some examples, the two-sensor device 1400 is implemented in a thin film device 1400', where a pulse-oximetry sensor chip 1404' (including both an infrared light source and photodetector is embedded within same thin film layer 1406' as a PVDF piezoelectric pressure sensor 1402'.

Figure 15:
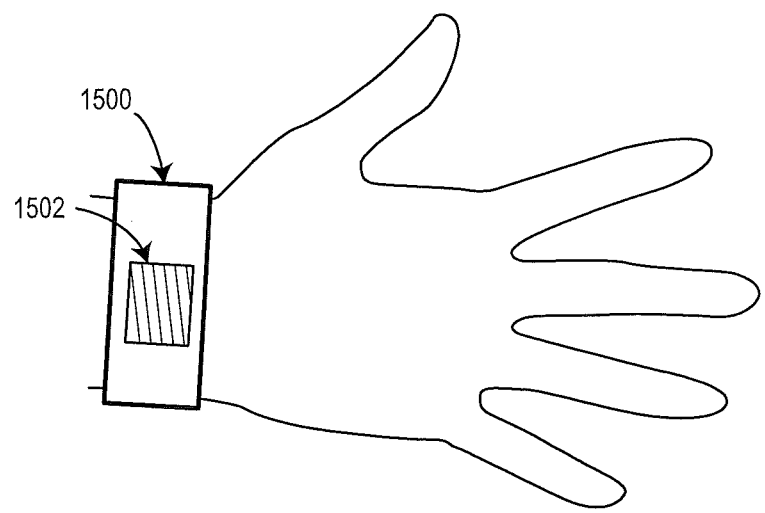
FIG. 15 illustrates an example wristband type device integrating a sensor assembly, such as the two sensor device illustrated in FIGS. 14A and 14B, in accordance with an example.

Further, although the two sensor device 1400 is illustrated as being attached to a patient's finger as a "stand alone" device, a device substantially similar to that of the two sensor device 1400 may be integrated into another wearable device or article. For example, as illustrated in FIG. 15, an example two sensor device 1502 may be integrated into a wristband type device 1500. The wristband type device 1500 may be a smartwatch, activity tracking device, or other device, and may include one or more components separate from the two sensor device 1400. The wristband type device 1500 may also include one or more power sources (not shown) to power the two sensor device 1502 and one or more wired or wireless communication interfaces (e.g., WLAN, Bluetooth, radio frequency, etc.) to communicate gather data or derived signals from the two sensor device 1502. This same form factor may be used on the ankle or other locations.

Figures 16A, 16B:
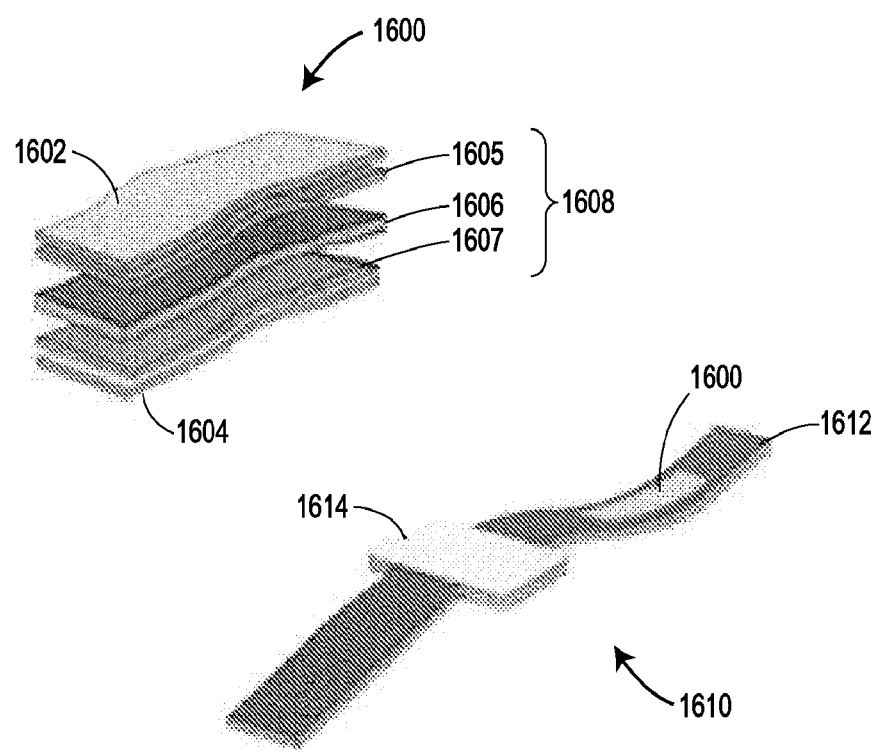
FIGS. 16A and 16B illustrate another example two sensor device formed of a piezoelectric sensor and pulse-oximetry sensor, in accordance with an example.

FIGS. 16A, 16B, 17, and 18 illustrate other example sensors, with similar functional, structural, and operational features as described above regarding the sensor 200, with some changes. FIG. 16A illustrates a sensor 1600 having a first encapsulating layer 1602 and a second encapsulating layer 1604, similar to layers 202 and 204, sandwiching a piezoelectric layer 1606 and two electrode layers 1605 and 1607 that form an embedded pressure sensor 1608. The sensor 1600 may further include an embedded pulse-oximetry sensor (also referred to herein as a "PPG sensor" for convenience purposes, not shown). Additional sensors may be included in the sensor 1600, and in particular sandwich between the layers 1602 and 1604, including temperature sensors, motion sensors, actigraphy sensors, galvanic skin response sensors, impedance sensors, or any combination thereof.

The sensor 1600 may be configured as a wearable device like that of the sensor 200. FIG. 16B illustrates the sensor 1600 in a wearable device 1610, having an attachment band 1612 for affixing to a subject, such as for affixing to a finger, in similar manner to that of sensor 200. The wearable device 1610 further includes a controller stage 1614, which includes one or more processes and one or more memories. The controller stage 1614 is configured to perform various processes described herein, such as those described in reference to signal-processing device 802, controller 300, as well as the vascular radius, vascular resistance, and vascular stiffness determinations described herein.

Figure 17:
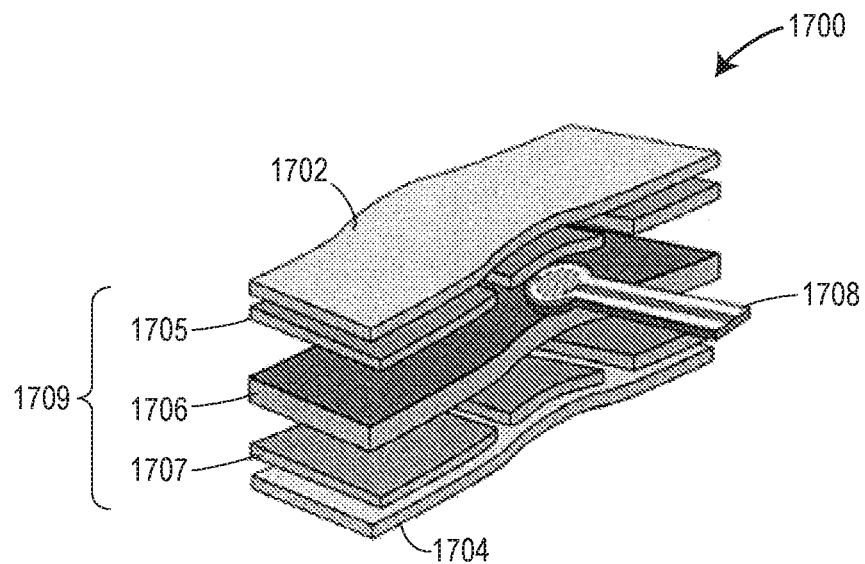
FIG. 17 illustrates yet another example two sensor device formed of a piezoelectric sensor and pulse-oximetry sensor that may be used for determining, inter alia, absolute blood pressure, in accordance with an example.

FIG. 17 illustrates another example sensor, sensor 1700, having encapsulating polymer layers 1702 and 1704. Sandwiched therebetween is a piezoelectric layer 1706 and two electrode layers 1705 and 1707 that form a first embedded pressure sensor 1709. A pulse-oximetry sensor (not sure) may also be included, either sandwiched between the layers 1702 and 1704 or positioned on the exterior of one of the layers. In the illustrated example, the sensor 1700 includes second embedded pressure sensor which is a separate low-bandwidth, high-accuracy pressure sensor (or tension sensor) 1708 positioned and configured to provide a measure of absolute changes in blood pressure, rather than relative changes. In some examples, the sensor 1708 is a piezoelectric sensor. For example, the sensor 1708 may be positioned and configured to provide a baseline pressure measurement against which the piezoelectric sensor 1706 is compared by a signal processing device. The signal processing device determines, from the comparison, a pressure in a subject's finger, due to blood flow, and thus determines the blood pressure for the subject over the vascular region under examination. Moreover, by providing the output of both pressure sensors to a controller, the signal processing device can determine an absolutely blood pressure for a patient, instead of a relative change in blood pressure over time.

Figure 18:
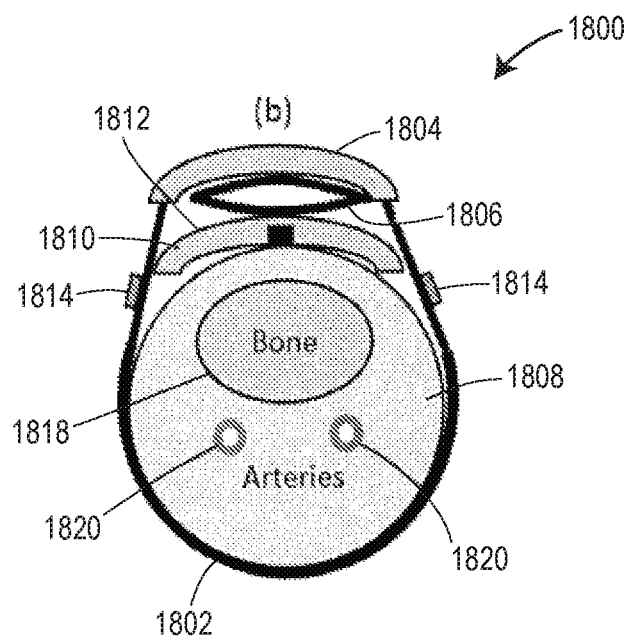
FIG. 18 illustrates yet another example two sensor device formed of a piezoelectric sensor and pulse-oximetry sensor, in accordance with an example.

FIG. 18 illustrates an example sensor, sensor 1800, that may be mounted to the finger of a subject as a wearable sensor. The sensor 1800 includes a PVDF laminate layer 1802 extending from an upper polymer retention layer 1804. A tension modulating actuator 1806 is mounted within a recess of the polymer layer 1804 and provides a resistance against which changes in pressure applied to the PVDF laminate layer 1802 by a subject's finger 1808 may be modulated against. In the illustrated example, a finger engagement polymer layer 1810 is positioned for contact with the subject's finger 1808 and which has an upper actuation surface 1812 that engages and modulates against the actuator 1806 for sensing changes in pressure in the finger. Tension sensors 1814 are provided on an outer surface of the PVDF laminate layer 1802 to sense changes in tension in the laminate layer 1802, where a signal-processing device determines a change in pressure from the measured changes in tension. Further, the sensor 1800 includes a pulse-oximetry sensor 1816. An example orientation of the finger 1808, for positioning of bone 1818 and arteries 1820 is provided by way of example. The sensor 1800 is operable in different orientations on the FIG. 1808.

Figure 19:
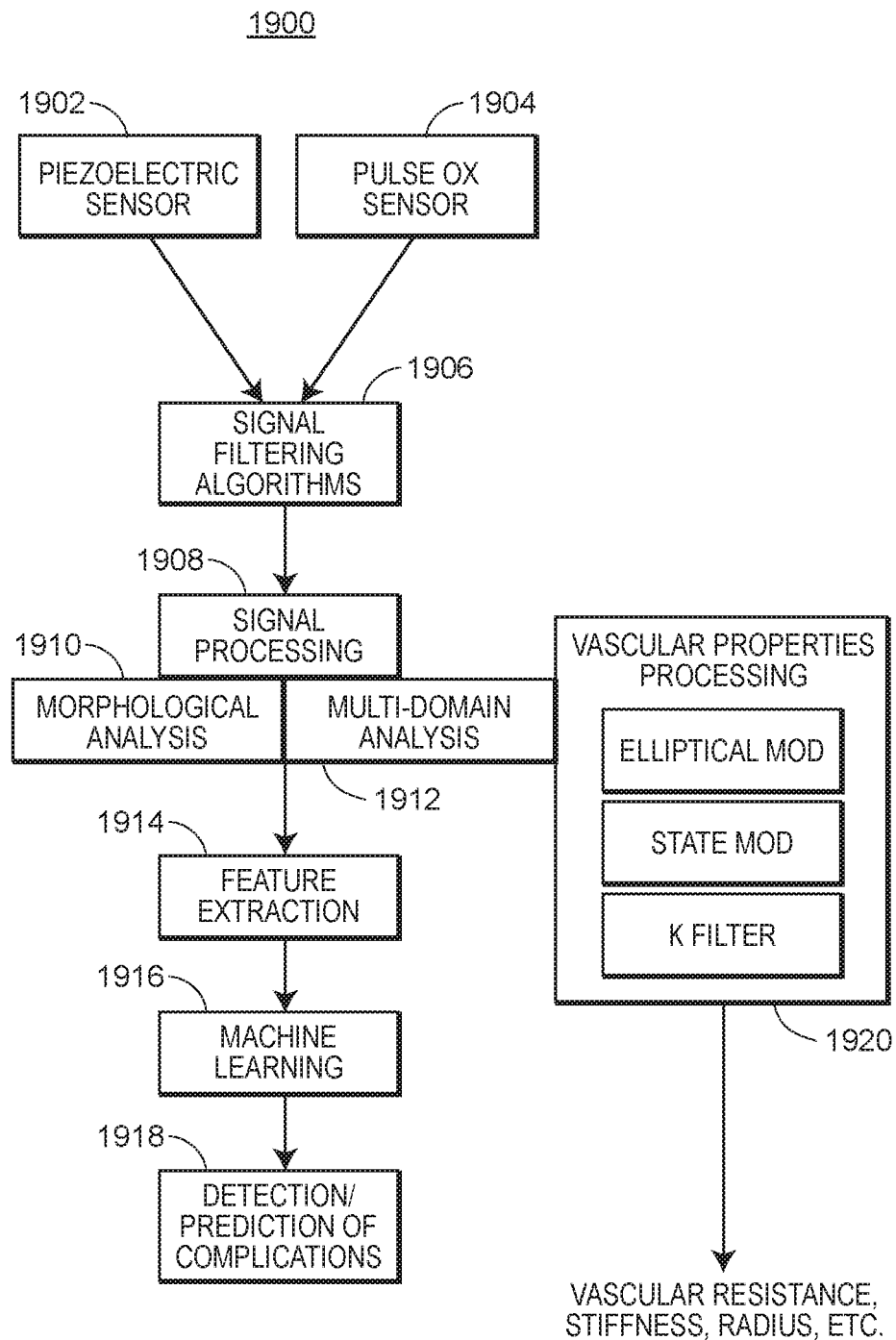
FIG. 19 is a flow diagram of operation of a signal processor in determining vascular resistance, vascular stiffness, and/or vascular radius, in accordance with an example implementation of FIG. 1.

The sensor devices herein may be implemented to determine vascular radius and systemic vascular resistance through the use of a vascular resistance controller that analyzes sensor data using developed vascular resistance models. FIG. 19 illustrates an example process diagram 1900 of operation of vascular resistance processing system, as may be implemented using the system 800, and having similar operation, in parts, to the processes 400 and 500 in FIGS. 5 and 6, such that like reference numerals are used in placed. The process diagram 1900, however, further includes the ability to determine vascular resistance or vascular stiffness.

In the illustrated example, one sensor 1904 is a PPG sensor. The PPG sensor 1904 senses a change in artery volume, which the PPG sensor 1904 detects by illuminating the skin of a subject at a sample region with the light from a light-emitting diode (LED) and then measuring the amount of light transmitted to a photodiode on an opposing side of the sample region. The photodetector converts light energy into an electrical current, which may be provided to a low noise electronic circuitry that, in some examples, includes a transimpedance (current-to-voltage) amplifier and filtering circuitry. A high pass filter may be used to reduce the size of the dominant direct current (DC) component and to enable the pulsatile alternating current (AC) component to be amplified. A low-pass filter may be used to remove the unwanted higher frequency noise such as electric interference (i.e. 60 Hz noise).

The voltage output of the PPG sensor 1904 is proportional to the change of the artery's volume. However, due to the transimpedance amplification and need for high-pass filtering to obtain the time-varying component of the light signal, conventionally-speaking PPG sensors do not provide long term tracking of mean absolute arterial volume, but rather respond to short term fluctuations in arterial volume during cardiac cycles. In effect, changes in volume are convoluted with amplifier and filter dynamics, which include a differentiation, then integrated to return the relative volume fluctuations. As a result, we developed a model for determining vascular resistance based on measurements from the pulse-oximetry sensor. For the model, we applied a model of PPG voltage output, $u_{PPG}$, as:

$$u_{PPG} = K_{PPG} \int h_{PPG} * V_i dt = K_{PPG} \int h_{PPG} * \pi r_i^2 L_{PPG} dt \quad (1)$$

where $K_{PPG}$ is the gain of the PPG sensor, $h_{PPG}$ is the linear dynamic filter response, and $V_i$ is volume of oxygenated blood between the LED light source of the PPG sensor and the photodetector. The volume, $V_i$, can alternatively be related to the inner radius of the artery $r_i$ and length of artery illuminated by the PPG, $L_{PPG}$. The length of the artery under the PPG sensor 1904 is assumed constant. It is noted that while a linear relationship between PPG sensor output voltage and vascular volume is applied in these examples, in other examples, a non-linear and/or time-varying relationship between PPG sensor output voltage and length may be applied.

In the illustrated example, the other sensor of the system 1900 is the piezoelectric (e.g., a PVDF) pressure sensor 1902. As with other examples herein, the pressure sensor 1902 may have a ring configuration; and each of the sensors 1904 and 1902 may be configured as part of the same wearable sensor device. The operation of the signal filtering algorithms 1906, signal processing 1908, morphological analysis 1910, multi-domain analysis 1912, feature extraction 1914, machine learning 1916, and detection/prediction processes 1918 may be the same as similar features illustrated in FIGS. 5 and 6. Additionally, the process 1900 includes a vascular resistance/vascular stiffness determination process 1920, as described herein.

Figure 20:
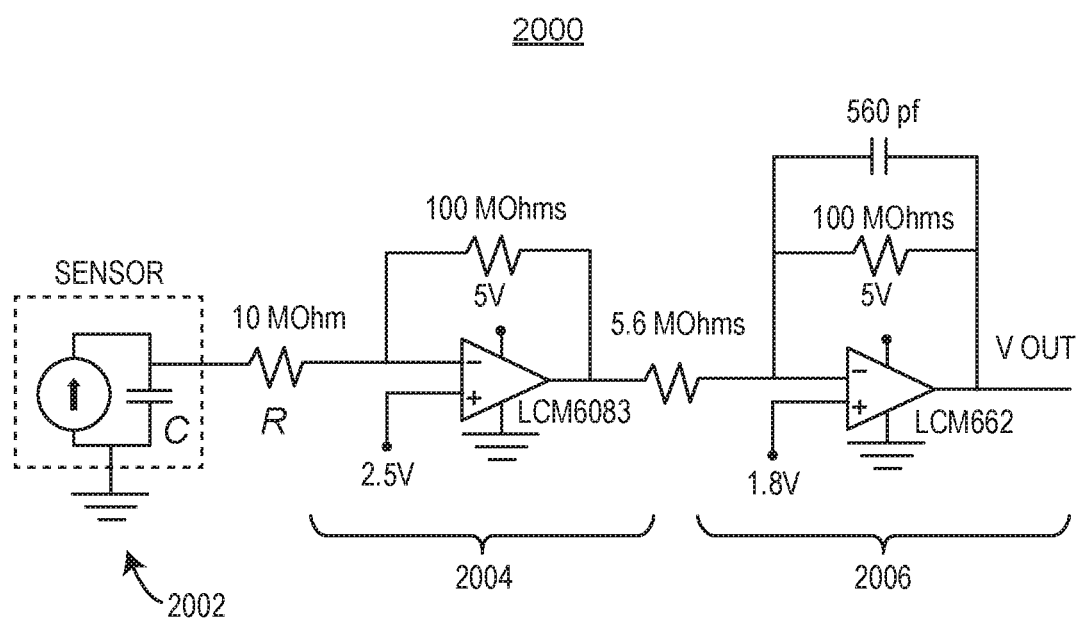
FIG. 20 is a schematic of an example circuit model of a piezoelectric pressure sensor, in accordance with an example.

In the electrical domain, the piezoelectric sensor 1902 can be modeled as a charge source in parallel with the sensor's capacitance. A high impedance charge mode amplifier may be used to convert electrical charge to voltage. FIG. 20 illustrates an example circuit schematic 2000 of operations of the piezoelectric pressure sensor 1902 (also termed "PVDF sensor 1902"). The sensor schematic 2000 illustrates an example PVDF sensor 2002. To compensate for low current from the PVDF sensor 2002, i.e., current measured around 1-5 nA, the schematic 2000 further included an stage amplifier 2004, followed by a low pass filter stage 2006 that helps minimize electrical interference and high frequency noise.

Charge, q, generated on the PVDF sensor 1902 is given by:

$$q = d_{31} E A \varepsilon_1 \qquad (2)$$

where $d_{31}$ is the piezoelectric strain coefficient from tangential strain to charge displacement in the electrode direction, is the elastic modulus of the PVDF, A is the surface area of the PVDF, and $\varepsilon_1$ is the tangential strain in the PVDF layer. In the model of Expression (2), compressive piezoelectric response (i.e., piezoelectric strain coefficient in the axial or electrode direction, $d_{33}$) and coupling effects are neglected as small compared to the dominant response from hoop stress around the ring formed by the sensor. In other examples, e.g., of other piezoelectric materials, the charge may be generated to a greater degree by other piezoelectric axes (i.e., $d_{33}$ piezo coefficient).

FIG. 20 shows the combined electrical model of the PVDF sensor 1902 and sensing circuit 2000, with resulting transfer function, $H_{PVDF}(s)$:

$$H_{PVDF}(s) = \frac{s}{RCs+1} \cdot \frac{K_{amp}\omega_{LPF}}{s+\omega_{LPF}} = \frac{18s}{(s+6)(s+178)} \qquad (3)$$

where R is the input resistance to the sensing circuit 2000 (e.g., 10 MOhm), C is the PVDF sensor capacitance, $K_{amp}$ is the net amplifying circuit gain, and $\omega_{LPF}$ is a low pass filtering frequency set by the second stage of the sensing circuit.

Even with a relatively large amplifier resistance used to maintain a high input impedance for the small capacitance and charge generation of the PVDF material, the RC time constant of the sensor 2000 is small, and its associated corner frequency in Expression (3) is much higher than frequencies of interest in the pressure waveform. Thus, the raw voltage output of the sensing circuit 2000 is approximately proportional to the derivative of the charge generated or pressure.

In some examples, the present techniques account for variation in pressure experienced by the PVDF sensor 1902, for example, by integrating the convolution of the time-varying charge with the amplifier dynamic response from Expression (3), $h_{pvdf}$, to produce a the final PVDF sensor output used for analysis, $u_{pvdf}$:

$$u_{PVDF} = \int h_{PVDF}(t) * q(t) dt. \qquad (4)$$

The integration is used because the small charge amplitude and relative impedance of the sensor result in a high-pass filter cut-off frequency much higher than the frequency of cardiac cycles; integration returns this to an output approximately proportional to blood pressure, but mediated by intervening tissue, as discussed below. As described above, in other examples, a time-varying and/or nonlinear gain relationship may be used instead, through the use of other circuit models or if through the use of other piezoelectric materials.

The piezoelectric sensor 1902 responds predominantly to tangential stress or strain in the PVDF sensor of a wearable device, as the PVDF sensor stretches in response to fluctuations in pressure and volume inside the underlying arteries. However, the pressure experienced by the PVDF sensor 1902 may not be identical to the underlying arterial pressure, due to additional tissue dynamics.

Figure 21A:
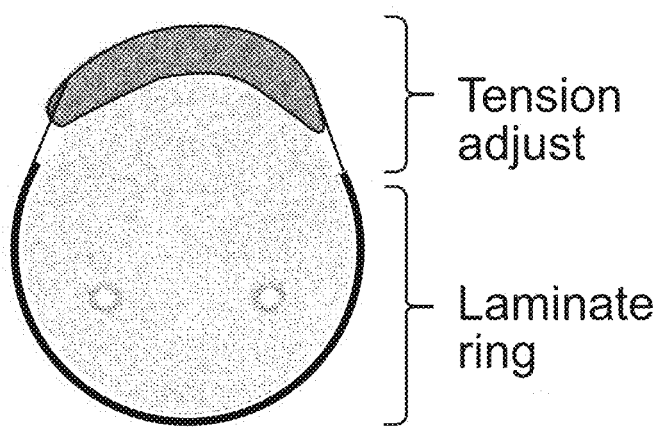
FIGS. 21A-21C illustrate parameters of a mechanical model of a vascular region, in particular a blood vessel, as may be used in determining vascular properties, in accordance with an example.
Figure 21B:
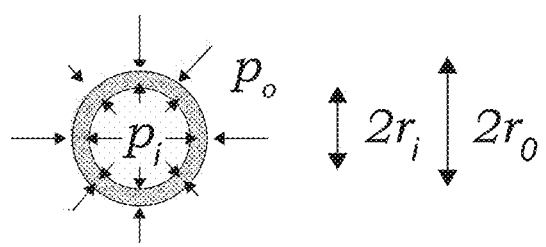
Figure 21C:
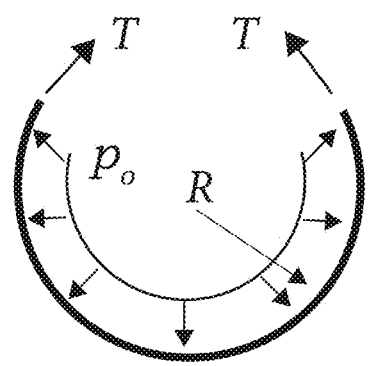

To approximate this behavior, we developed a mechanical model that supported dynamic modeling of viscoelastic effects seen to be important to artery and sensor behavior. The mechanical model was based off of the configuration and values in FIGS. 21A-21C. The mechanical model included a thick-walled cylinder modeling the artery, including a nonlinear elastic modulus approximation, other soft tissue and skin approximated as a compressible volume, and a linear elastic ring approximation for the sensor, as shown in FIGS. 21A-21C. A basic assumption of mechanical model was that the artery can be treated as straight and the cross-sectional properties of tissue and bone display minimal changes over the width of PVDF sensors (<1 cm) compared to overall artery and limb length. The peripheral artery is approximated using a linear thick-walled elastic tube model:

$$\frac{\delta r_i}{\bar{r}_i} = \frac{1}{E(r_i)}[f_{ii}(\bar{r}_i,\bar{r}_o)\delta p_i - f_{io}(\bar{r}_i,\bar{r}_o)\delta p_o] \qquad (5)$$

$$\frac{\delta r_o}{\bar{r}_o} = \frac{1}{E(r_o)}[f_{oi}(\bar{r}_i,\bar{r}_o)\delta p_i - f_{oo}(\bar{r}_i,\bar{r}_o)\delta p_o] \qquad (6)$$

where $\bar{r}_i$ and $\bar{r}_o$ are the average inner and outer radius of the artery wall, $\delta r_i$ and $\delta r_i$ are their variation in time during a cardiac cycle, E is artery elastic modulus, $\delta p_i$ is pressure change inside the artery, and $\delta p_o$ is pressure change as experienced by the sensor, which may differ from $\delta p_i$ due to internal stresses in the artery walls and compressibility of intervening tissue but is assumed to approximately isotropically resist arterial expansion. $f_{ii}$, $f_{oi}$, $f_{io}$, and $f_{oo}$ are functions for circumferential stress at the inner (i) or outer (o) radius of the artery. It should be noted that $f_{ii}$, $f_{oi}$, $f_{io}$, and and $f_{oo}$ are not independent parameters, but are standard functions of $\bar{r}_i$ and $\bar{r}_o$ for a uniform thick-walled elastic tube.

The PVDF sensor 1902 response was modeled as thin-walled cylinder subject to approximately uniform pressure from the underlying tissue ($p_o$) and an initial tension, T, in the sensor. Perturbations of the sensor radius, $\delta R$, from its nominal radius, $\bar{R}$ were modeled in the form:

$$\delta R = \frac{2\bar{R}^2}{E_s t}\delta p_o - \frac{\bar{R}}{E_s t}\delta T \qquad (7)$$

where $E_s$ is the composite modulus of the PVDF and polyimide layers, t is the sensor band thickness, and $\delta T$ represents any external perturbations to tension in the sensor, though in this study T is generally held constant.

The result is an expression of the relationship between artery radius, $r_o$, and the external pressure from the skin felt on a piezoelectric sensor:

$$\pi(\overline{R}+\delta R)^2 = 2\pi(r_o+\delta r_o)^2 + V_o - \gamma\delta p_o \quad (8)$$

where $V_o$ is the nominal cross-sectional tissue area enclosed by the sensor, excluding arteries, $\gamma$ is a measure of net intervening tissue compressibility. Two major arteries are known to be present under the appendage being monitored. Combining Expressions (5)-(8) and assuming external tension, T, is fixed, a nonlinear function relating sensor pressure perturbations, $\delta p_o$, to artery perturbations, $\delta r_o$, can be obtained:

$$\pi\left(\overline{R}+\frac{2\overline{R}^2}{E_s t}\delta p_o\right)^2 = 2\pi(r_o+\delta r_o)^2 + V_o - \gamma\delta p_o \quad (9)$$

Both the artery and skin exhibit viscoelastic behavior that leads to hysteretic behavior during phases of increasing versus decreasing pressure during cardiovascular cycles. Experimental comparison of the PVDF sensor response to blood pressure measurements using a finger cuff, in which pressure is regulated to maintain a constant arterial volume, showed a clear hysteresis in piezoelectric signal, consistent with hysteresis arising from viscoelastic effects in tissue. To capture this behavior, a simple viscoelasticity model was added to the mechanical model of Expressions (8) and (9). In an example, a Standard Linear Solid Model was used that combines Maxwell model dynamics and a Hookean spring in parallel to relate a stress, $\sigma$, to a strain, $\varepsilon$; a viscous material is modeled as a spring and a dashpot in series, both of which are in parallel with a lone spring. The resulting module can be expressed as:

$$\frac{d\varepsilon(t)}{dt} = \frac{\frac{E_2}{\eta}\left(\frac{\eta}{E_2}\frac{d\sigma(t)}{dt}+\sigma(t)-E_1\varepsilon(t)\right)}{E_1+E_2} \quad (10)$$

where $\sigma$ is the applied stress, $E_1$ and $E_2$ are elastic moduli describing the tissue, $\eta$ is a viscoelasticity coefficient, and $\varepsilon$ is the strain. Defining $\varepsilon(t)=\delta r_0/\overline{r}_o$ and $\sigma(t)=f_{oi}\delta p_i - f_{oo}\delta p_o$ from the thick wall cylinder model and combining Expressions (5), (8), and (10), a constitutive relation between arterial variation and inner and outer pressure under the PVDF sensor 1902 can be obtained accounting for viscoelasticity:

$$\frac{d\varepsilon}{dt} = \frac{\left(f_{oi}\frac{dp_i}{dt}-f_{oo}\frac{dp_o}{dt}\right)+\frac{E_2}{\eta}(f_{oi}\delta p_i - f_{oo}\delta p_o)-\frac{E_2}{\eta}E_1\varepsilon}{E_1+E_2} \quad (11)$$

Changes of inner pressure may also be related to other variables by an alternative arrangement of (11), that is as:

$$\frac{dp_i}{dt} = \frac{E_2}{\eta}\frac{\left(f_{oo}\frac{\eta}{E_2}\frac{dp_o}{dt}+f_{oo}\delta p_o - f_{oi}\delta p_i\right)+\frac{\left(\frac{\eta(E_1+E_2)}{E_2}\frac{1}{r_o}\frac{dr_o}{dt}+E_1\frac{\delta r_o}{r_o}\right)}{f_{oi}}}{f_{oi}} \quad (12)$$

It should be noted that assignment of viscoelastic effects to the artery alone, computed in terms of $r_o$ is done to simplify model behavior, but effectively lumps in viscoelastic behavior from other sources, such as skin and intervening tissue, when model identification is performed. An alternate approach would be add viscoelastic effects as related to entire limb radius, R, and conceptually should be possible to implement with nearly equivalent results. Practically, placing the primary effect at the artery has been observed to give better matching of hysteresis trends versus measured SVR.

Figure 22:
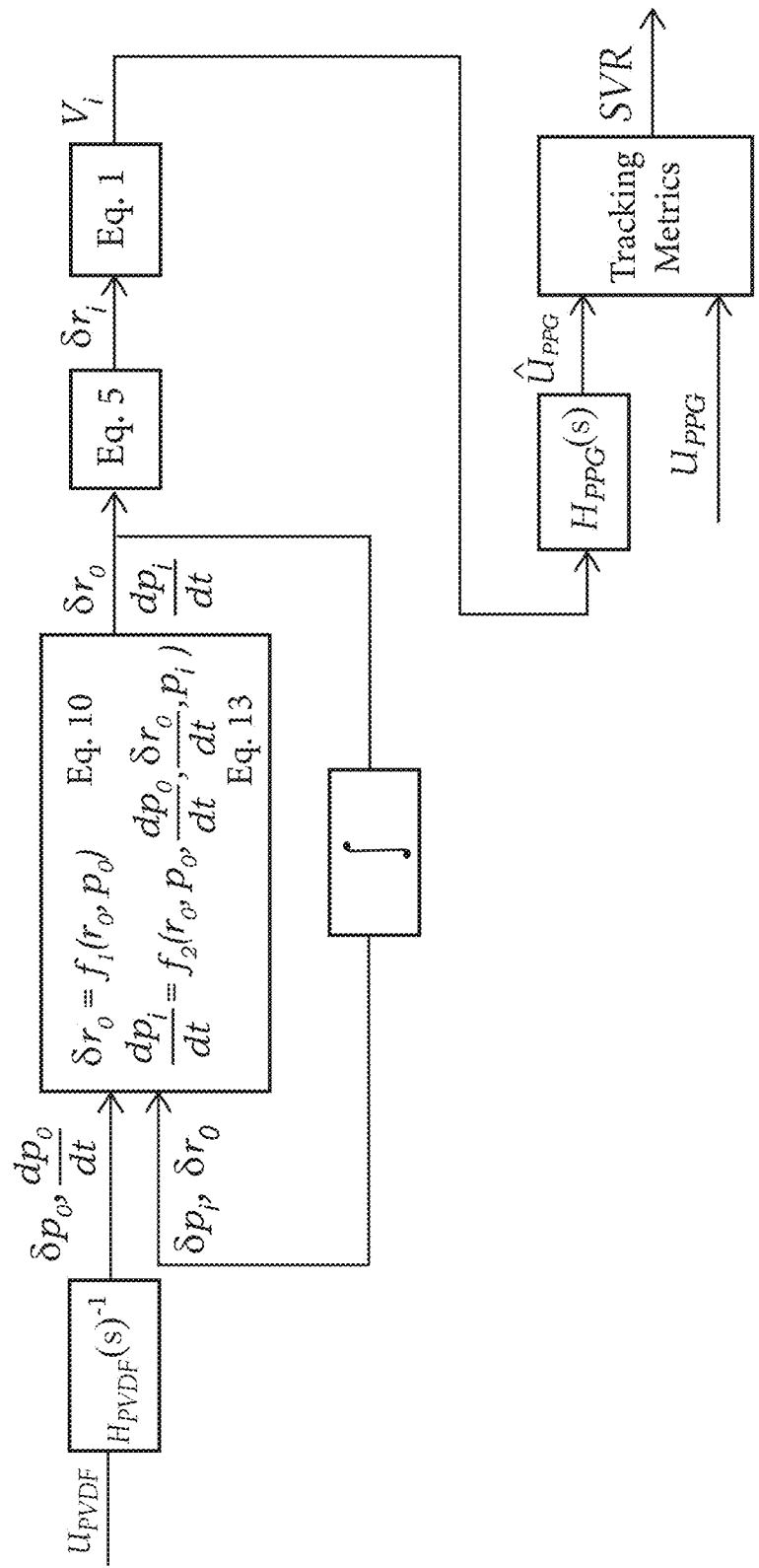
FIG. 22 illustrates an example sensor computation model that may be used to determine vascular resistance and/or vascular stiffness, in accordance with an example.

To summarize the sensor model, two independent equations are present: a static relationship relating perturbations in pressure on the PVDF sensor 1902 to arterial radius ($\delta p_o$ vs $\delta r_o$) (e.g., Expression (8) and a dynamic equation for either artery radius or internal pressure (e.g., Expressions (11) or (12)) incorporating basic viscoelastic behavior, with variables $\delta p_i$, $\delta p_o$, and $\delta r_o$. Once $\delta p_o$ can be measured, as with the PVDF sensor 1902, this is sufficient to solve for the other two variables. FIG. 22 illustrates an example implementation of the sensor computation model, for example, that may be applied at process 1920 in determining vascular resistance and/or vascular stiffness. For example, during implementation, a piezoelectric sensor voltage, $\mu_{PVDF}$, is measured and used to infer changes in external pressure, $p_o$, at the process 1920, which then uses this value to calculate perturbations in internal artery pressure, $p_i$, and radii, $r_i$ and $r_o$ via the model of FIG. 22 implemented by the process 1920. These estimates are used to predict what changes in internal artery volume, $V_i$, would be at the nominal artery radius, along with an anticipated PPG sensor output, $\hat{u}_{PPG}$.

The process 1902 may compare the output of the model in FIG. 22 to the actual PPG sensor output, $u_{PPG}$, to estimate systemic vascular resistance, SVR.

Figures 23A, 23B:
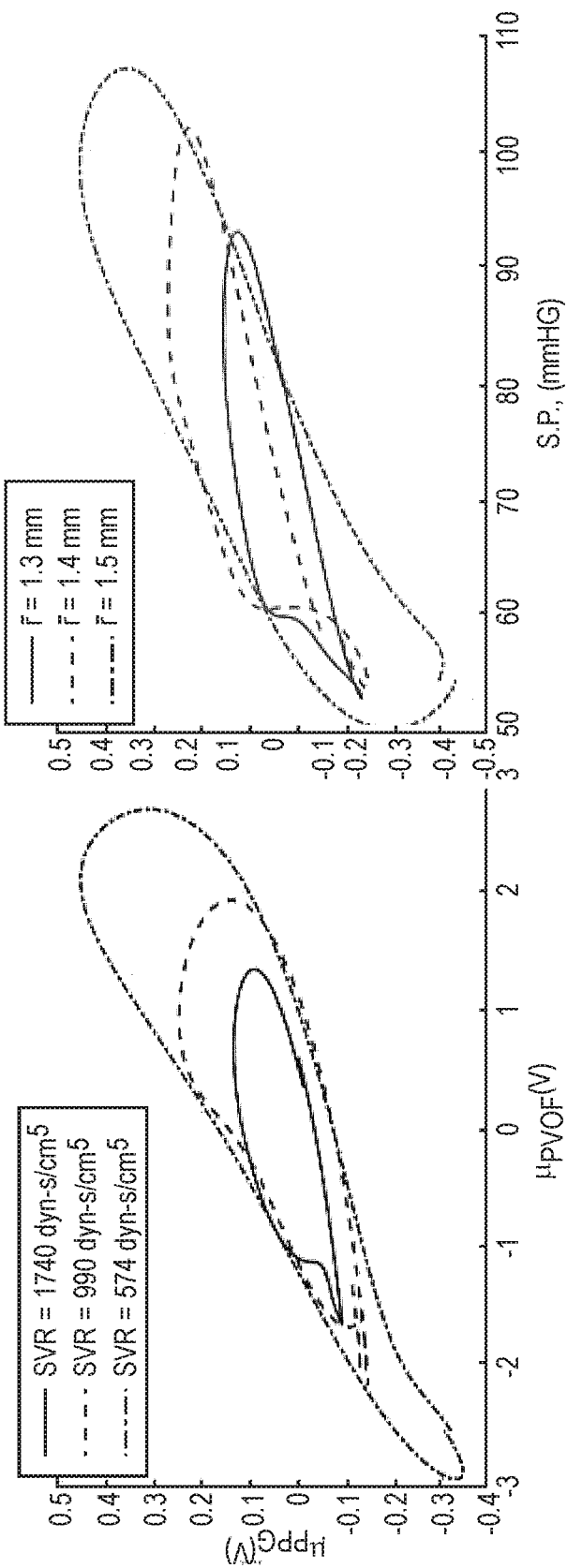
FIGS. 23A and 23B are plots of application of an elliptical model comparison of a pulse-oximetry sensor data to a pressure sensor data, with FIG. 23A showing an elliptical (hysteresis) comparison of experimental test data and FIG. 23B showing an elliptical (hysteresis) comparison of predicted data, in accordance with an example.

Neither the PPG sensor 1902 nor the piezoelectric sensor 1904 provide absolute measurement of arterial radius or pressure (as compared to the sensor configuration of FIG. 17 which does provide absolute values), but rather time-varying perturbations from those signals' average values. However, the sensors' relative amplitudes and dynamic responses (i.e., relative hysteresis) remain dependent on artery radius changes. FIG. 23A is a plot of PPG sensor data vs PVDF pressure sensor data for experimental tests on swine data, i.e., collecting data from swine arteries, at various vascular resistance levels. FIG. 23B is a plot of predicted PPG sensor vs. PVDF sensor response data for different arterial radii corresponding to the SVR conditions of FIG. 23A. As is apparent, the empirical data of FIG. 23A is in strong agreement with the model data we developed and tested for FIG. 23B.

To track vascular resistance in real time, the data from both the PPG sensor 1902 and the PVDF pressure sensor 1904 are collectively analyzed at the process 1902. In some examples, the process 1902 compares the sensor data from both sensors to determine an elliptical fit over a sample, also termed a hysteresis technique of vascular resistance/stiffness determination.

Figure 24:
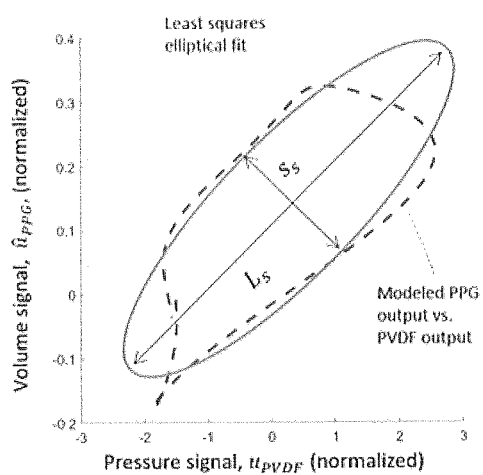
FIG. 24 illustrates an elliptical (hysteresis) comparison of a pulse-oximetry sensor data to a pressure sensor data, in accordance with an example.

At the process 1902, PPG sensor data and PVDF sensor data are compared and quantified through linear regression of a resulting PPG/PVDF hysteresis loop, e.g., taken over a number of cardiac cycles. During each cardiac cycle a comparison ellipse is generated, by the process 1920, for the best least squares fit of the hysteresis loop between the PPG sensor and the piezoelectric sensor outputs for both the measured (experimental) and the projected (hypothetical fixed radius) data, as shown in FIG. 24. A first feature correlated with invasive vascular resistance is the difference in projected and measured amplitude of the signals, measured using a long chord of the projected ellipse at a fixed model radius, $L_s$, and the long chord of the experimentally obtained ellipse, $L_e$. Using these measurements, a normalized vascular resistance, SVR, is estimated by the process 1920 applying the following expression:

$$\widehat{SVR}_{1,1} = 0.02(L_s - L_e) + 0.52 \quad (13)$$

with L being the long chord of an ellipse fit, where subscript s indicates the simulated PPG output given the current PVDF output and subscript e indicates the actual experimental output. Effectively, this metric is selected to capture the mismatch increased signal amplitude when arterial radius changes from baseline, while the ratio of PPG sensor output amplitude to PVDF sensor output amplitude remains approximately constant if only blood pressure changes at a fixed nominal arterial radius.

When SVR increases, observed experimental hysteresis is larger than that projected based on the model with constant nominal radius. Based on linear regression from the initial cycles of testing with swine 1, this is quantified by the process 1920 as:

$$\widehat{SVR}_{1,2} = -0.166(h_s - h_e) + 0.7 \quad (14)$$

where h is a hysteresis measurement obtained from:

$$h_{s,e} = \frac{L_{s,e} - S_{s,e}}{L_{s,e}} \quad (15)$$

where S is the short chord of the ellipse fit to the hysteresis loop. In this way, the process 1920 computes SVR from the output of the PPG sensor 1904 and the PVDF pressure sensor 1902.

The Expressions (13) and (14) are merely representative of the types of relationships that may be defined between PPG/PVDF waveform comparisons and arterial radius with the present techniques. Other relationships between PPG/PVDF waveform comparisons and arterial radius, vascular resistance, vascular stiffness, etc. may result from the computational processes herein.

Figure 25:
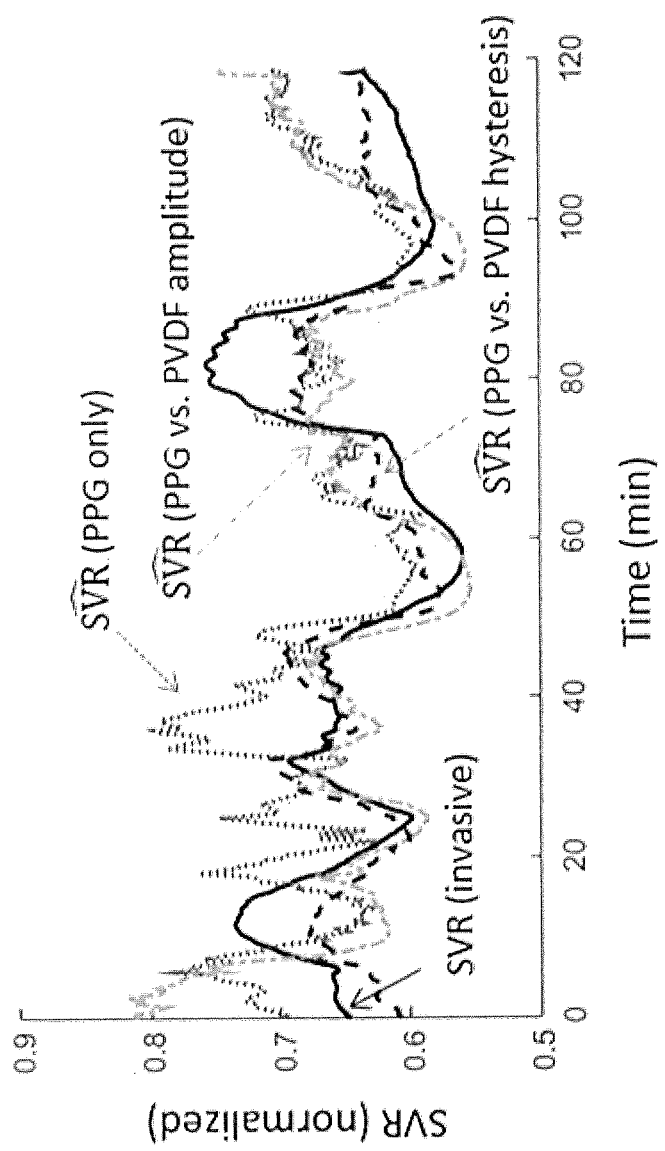
FIG. 25 is a plot of systemic vascular resistance determined from an elliptical (hysteresis) comparison of a pulse-oximetry sensor data to a pressure sensor data, in accordance with an example.

FIG. 25 illustrates example SVR values that were determined by the process 1920, using the PPG sensor vs. PVDF sensor hysteresis comparison described herein. Various plots are shown for SVR computed from the PPG sensor data only; SVR computed from dual PPG sensor and PVDF amplitude sensor data; SVR measured from an invasive, sub-surface measurement technique; and SVR computed from PPG sensor and PVDF sensor data according to the hysteresis technique of FIG. 24. While the SVR determination from the PPG sensor only and from the PPG vs. PVDF sensor amplitude both track the SVR invasive data (i.e., the reference data), over portions of the time frame, the SVR determined at the process 1920 by a hysteresis comparison of the PPG sensor data and the PVDF sensor data most accurately tract and thus demonstrate SVR determinations over time.

Additional modifications may be made to the processes applied at the process 1902 for SVR determination. For example, SVR determination could further include compensating for uneven pressure distributions on the PPG sensor and PVDF sensors. SVR determination could compensate for constraints on movement and pressure determinations from hard tissue in the sample region, such as bone in finger. Longitudinal mechanics of the artery wall extending along the length of the wearable device may also be compensated for in SVR determination. Viscoelastic behavior in the intervening tissue, i.e., tissue in the sample region other than arterial wall tissue. For example, in some implementations, the pulse transit time (PTT), e.g., the pulse time between a PPG sensor and a piezoelectric pressure sensor, is used. If the PTT deviates by more than a certain percentage (%) from its average value, sensor signals in that heartbeat are treated as noisy and given less confidence. In other examples, the fluid dynamics between the positions of PPG and pressure sensors may be taken into consideration, as well as additional dynamic states in the state model, including the effects of changing stiffness and/or radius in that part of the model, thereby expanding what can be extracted from the extended Kalman filter.

The present techniques include other approaches for determining SVR (i.e., alternative implementations of the process 1920), including tracking and determining arterial radius as a mechanism for determining vascular resistance.

In an example, an SVR determination process may include automated radius tracking using an extended Kalman filter (EKF). The extended Kalman filter is a technique for tracking states and/or parameters of dynamic systems. In an example herein, sensor data from both the PPG sensor 1904 and the PVDF sensor 1902 is provided to a state-space model that is used with extended Kalman filter to reduce signal error more quickly. In this example, the variables and signals in the models described above may be cast as either inputs or outputs in a nonlinear dynamic system expressed as:

State-Space Model

State vector:
$$\begin{bmatrix} x_1(t) \\ x_2(t) \\ x_3(t) \end{bmatrix} = \begin{bmatrix} r_o(t) \\ \delta p_i(t) \\ r_i(t) \end{bmatrix}$$

Input vector:
$$\begin{bmatrix} u_1(t) \\ u_2(t) \end{bmatrix} = \begin{bmatrix} \delta p_o(t) \\ \dfrac{dp_o(t)}{dt} \end{bmatrix}$$

Discrete nonlinear state-space model:

$$x_k = f(x_{k-1}, u_k) + w_k$$

$$z_k = h(x_k) + v_k$$

where $w_k$ and $v_k$ are process noise and measurement noise, and which are assumed to be independent, zero mean white Gaussian noise with covariances $Q_k$ and $R_k$, respectively. In this model $f(x_{k-1}, u_{k-1})$ is the nonlinear part of the state model. The inputs to the nonlinear dynamic system are thus quantities that can be extracted directly from the PPG sensor and PVDF pressure sensor outputs, provided properties of the PVDF wearable device and piezoelectric sensing circuit are well known. For example, the raw blood flow and pressure data from the PPG sensor and PVDF pressure sensors, respectively, can be provided to the nonlinear dynamic system. In the example of FIG. 19, in some examples, the output from the sensors 1902 and 1904 can be provided directly to the vascular properties process 1920, which then applies the extended Kalman filter process to produce vascular properties, such as vascular radius, vascular resistance and/or vascular stiffness, with less error and in a faster fashion. In some examples, the process 1920 determines other vascular properties applying other techniques herein such as using an elliptical model (hysteresis comparison), etc. to determine vascular radius, blood pressure, and/or cardiac vascular power. Furthermore, the states provided to the nonlinear dynamic system may be a combination of the original dynamic model for the system and predetermined parameters for system identification. The discretized nonlinear artery state model and output model are expressed by:

$$x_k = f(x_{k-1}, u_{k-1}) + w_k \qquad (16)$$

$$z_k = h(x_k) + v_k \qquad (17)$$

In some examples, the output models (i.e., Expressions (16) and (17)) are processed by in the signal processing device by the process 1920. The process 1920 provides these output models to an extended Kalman filter, also within the process 1920, that linearizes the nonlinear-state models for each new estimate of vascular radius, vascular resistance, and/or vascular stiffness, as the sensor data becomes available. As a result, in some examples, the extended Kalman filter algorithm outputs a desired vascular properties, such as outputting values of the inside radius of an artery (i.e., vascular radius). In some examples, the extended Kalman filter can be further used to output blood pressure and/or cardiac vascular power.

Figure 26:
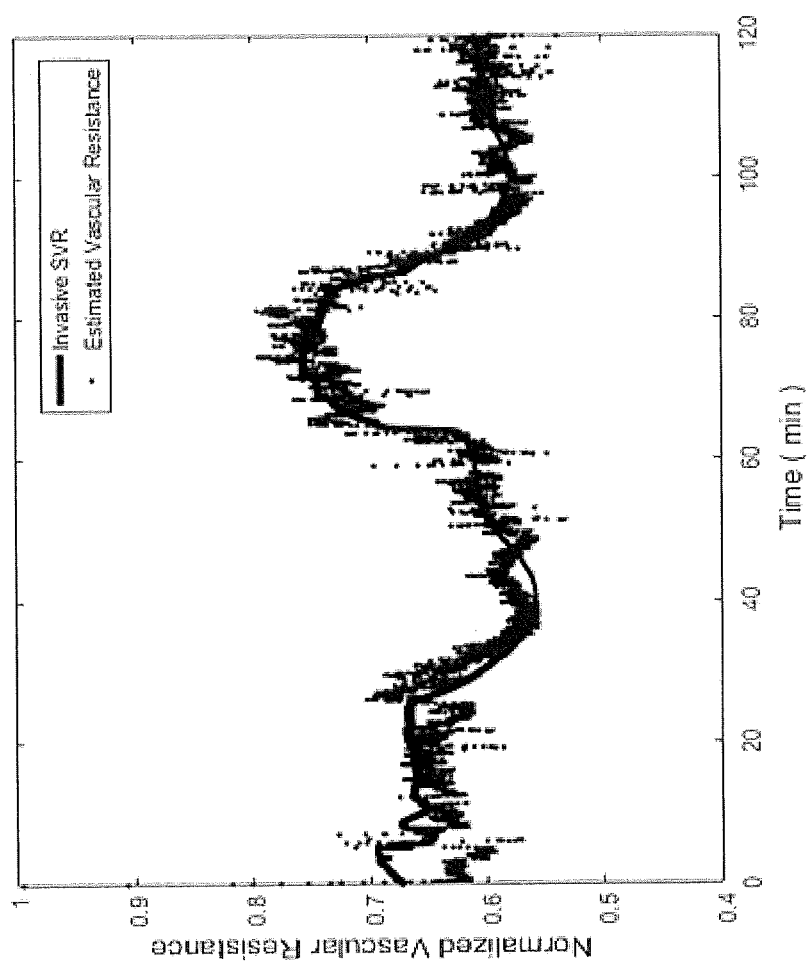
FIG. 26 is a plot of system vascular resistance determined by further application of an extended Kalman filter, in accordance with an example.

FIG. 26 illustrates an example implementation of an extended Kalman filter that produces the estimated vascular resistance at the PVDF pressure sensor and PPG sensor location. As shown, the estimated vascular resistance closely tracks the benchmark changes in radii, as measured using an invasive systemic vascular resistance measurement, thereby demonstrating the success of the Kalman filter process in determining arterial radius and, correspondingly, vascular resistance in a subject.

Figure 27:
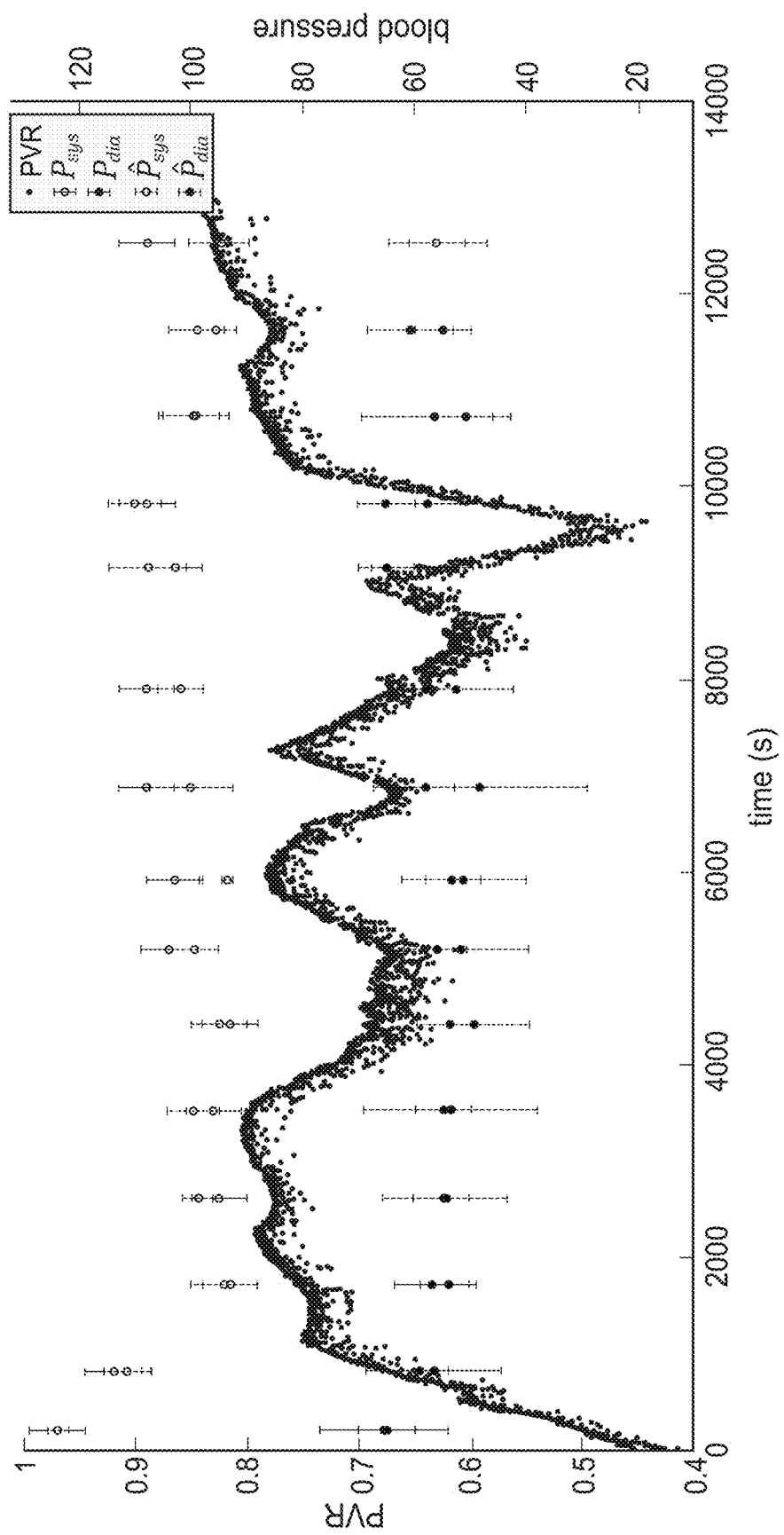
FIG. 27 is a plot of pulmonary vascular resistance (PVR) determined by application of extended Kalman filtered output vascular resistance and showing the PVR output correlating to systolic blood pressure, in accordance with an example.

Since blood pressure ($p_i$) is one of the states used in the Kalman filter process, the process can also track blood pressure without any changes to the extended Kalman filter. A sample result for a human subject is shown in FIG. 27, in comparison to the periodic (every 10-15 minute) measurements of diastolic and systolic blood pressure in a dialysis patient. The pulmonary vascular resistance (PVR)-labeled line shows the extended Kalman filtered output vascular resistance, which is more accurate data than that of conventional diastolic and systolic blood pressure.

Figure 28:
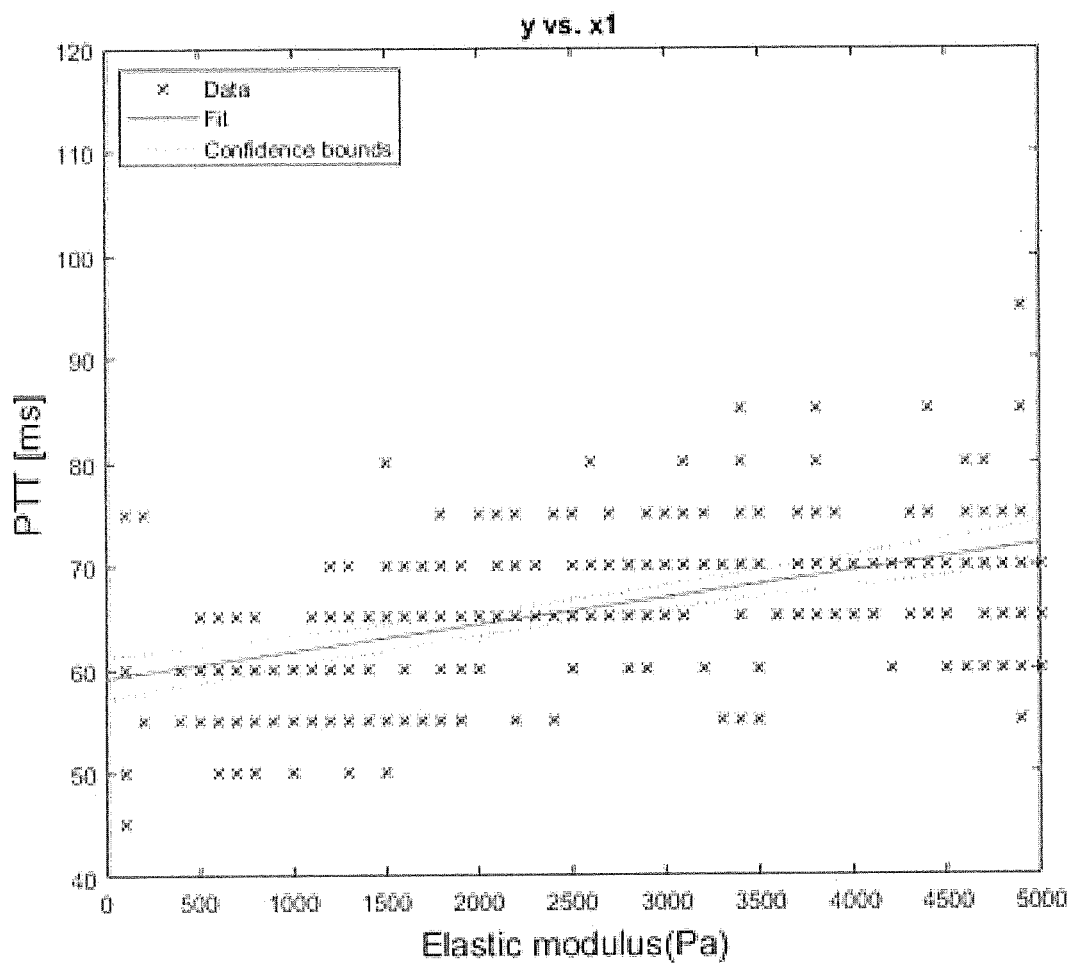
FIG. 28 is a plot of pulse transit time (PTT) versus elastic modulus showing PTT as an indication of vascular stiffness, in accordance with an example.

The Kalman filter process, being based on a state-space model, can be modified to include vascular stiffness (elastic modulus of the artery) as one of the states in the model. As shown in FIG. 28 there is a correlation between the stiffness extracted from the extended Kalman filter process and the stiffness inferred from pulse transit time, shown below; though there could be some confounding of the two measurements (they are both based on measurements from the piezo and PPG, but handled in very different ways).

Additionally, pulse transit time (PTT), measured either between the PPG sensor 1904 and the PVDF sensor 1902, or between some other earlier signal (ECG, sensor at the wrist or core) can also be used as a complementary indicator for vascular stiffness changes, or to compensate for finger motion artifacts. Large deviations in pulse transit time typically indicate finger movement and can be used in the reduce confidence of the sensor signals or to increase their noise density within the extended Kalman filter process, which we've seen improve vascular resistance estimation robustness, at the cost of a slower response time.

Thus, as shown, the present techniques also include a model and estimator based on an extended Kalman filter for tracking and determining vascular radius of peripheral arteries, making use of a mechanical model of arterial and tissue dynamics to account for varying response of a PPG and a piezoelectric pressure sensors. It is noted that other examples of the extended Kalman filter and other algorithms may be used, including for example, an unscented Kalman filter, least squares parameter identification, recursive autocorrelation adaptive models, and combinations thereof.

Further still, in some examples, the present techniques include determining an arterial power value using a sensor device. The wearable sensor devices herein can be implemented as a compliant finger ring structures, as described. The pressure sensors herein can be used to measure the work done by artery motion on the compliant ring structure and/or the power transmitted from the artery to the compliant ring structure. In an example, to measure work done, a controller may compute an integral of stress times strain in a wearable sensor device.

Figure 29:
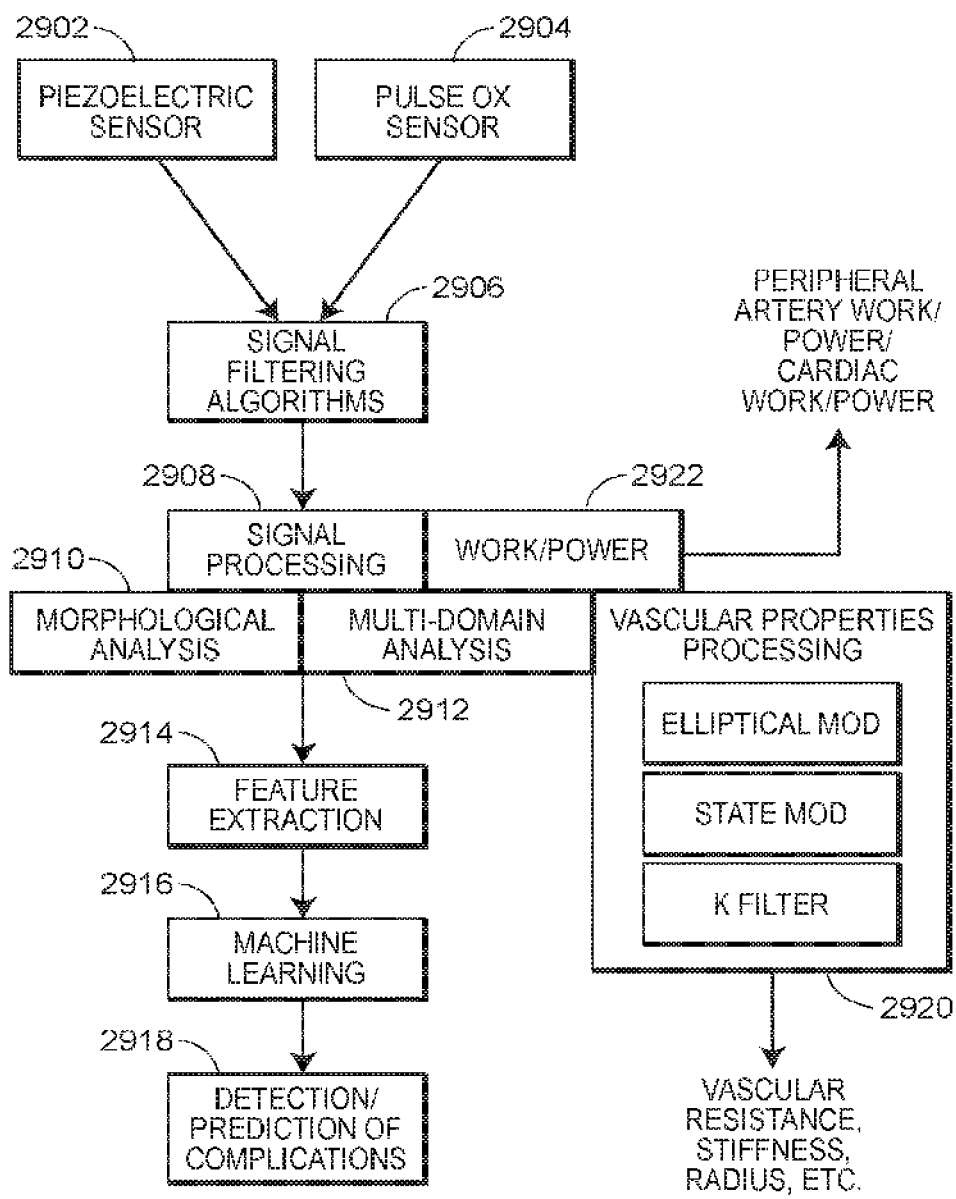
FIG. 29 is a flow diagram of operation of a signal processor in determining cardiac work and/or cardiac power, as well as optionally vascular resistance, vascular stiffness, vascular radius, in accordance with an example implementation of FIG. 1.

FIG. 29 illustrates a controller 2800 similar to that of FIGS. 5 and 19, using similar elements to those described above, and further including a work/power processor 2922 that collects data from a piezoelectric pressure 2902 and a PPG sensor 2904 (and through optional processing stages 2906 and 2908) determines a peripheral artery work or power. To determine the work/power value, the process 2922 may determine the work/power as proportional to the square of the charge generated in the piezoelectric sensor, for example. The proportionality may be determined by material properties and dimensions of the overall wearable sensor (i.e., the compliant ring structure) and the piezoelectric material used to form the sensor, as stored and applied by the process 2922.

To measure power exerted by a subject's finger, the work may be differentiated at the process 2922 to determine the power, or the power may be directly computed from the voltage output of the piezoelectric element, which is proportional to rate of change of pressure, multiplied by the amount of deformation in the compliant ring structure, again with a proportionality constant determined by material properties and dimensions. Commonly, the signal processor calculates power only for the expansion period of the artery during a cardiac cycle. This calculation is a reflection of cardiac vascular power or cardiac output and is useful as a reflection of deteriorating or improving cardiac function.

Figure 30:
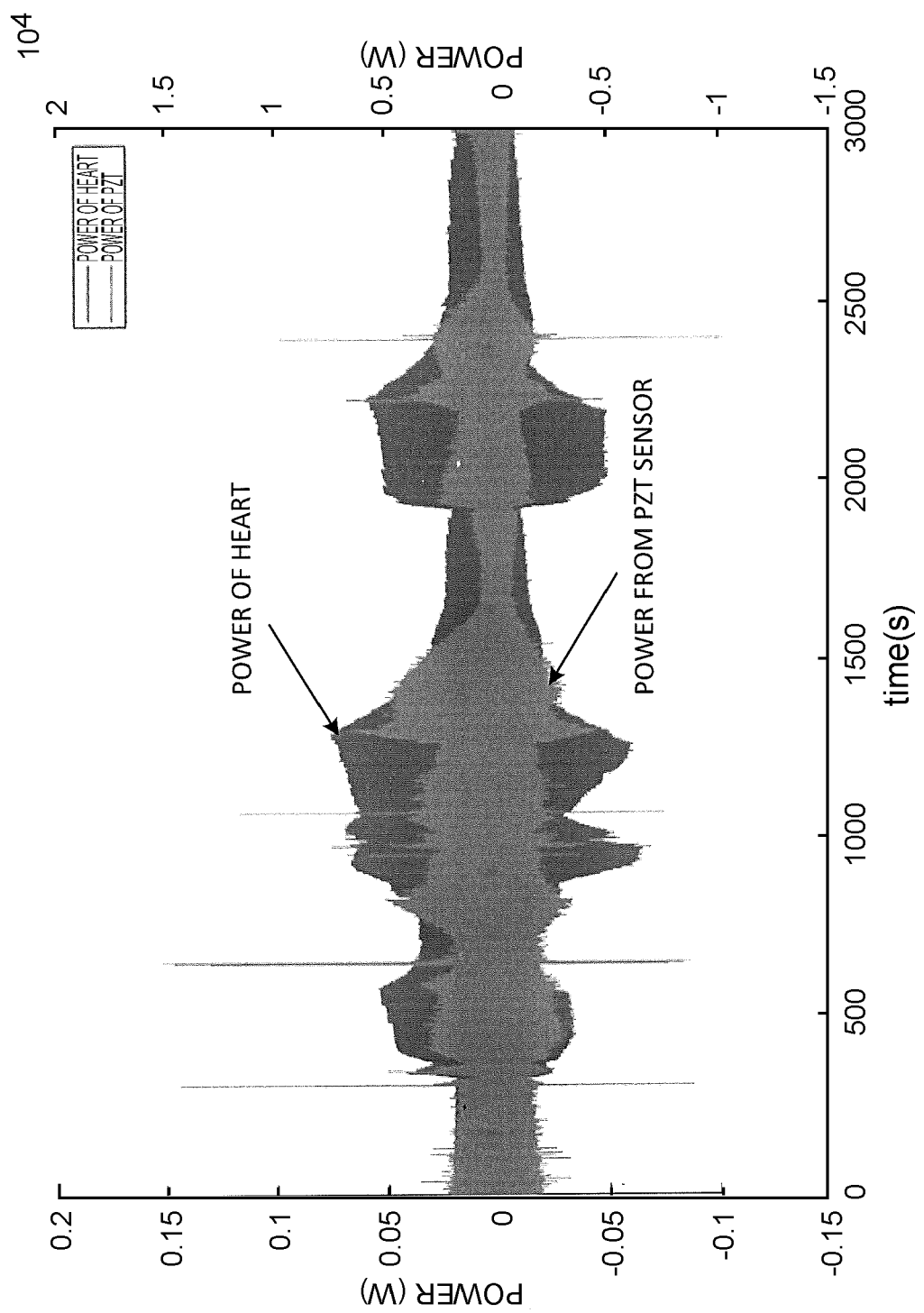
FIG. 30 is a plot of cardiac power as determined for an output of a pressure sensor, in accordance with an example.

A sample comparison of power 3002 measured at the peripheral artery using a piezoelectric pressure sensor to the power output 3004 of the heart in a swine subject measured invasively from cardiac output and pulse pressure, is shown in FIG. 30. Changes in power output from the piezoelectric PPG sensor 2902 is compared against changes in power output of the heart in swine subjects (as calculated by cardiac output times pulse pressure), but with cross-sensitivity to changes in arterial radius also measured using the ring, and with characteristic dynamic effects.

To determine vascular resistance from the arterial radius, a vascular resistance/stiffness process 2920 that receives the work and/or power data from the process 2922 is provided. Whether calculating vascular resistance or stiffness, the determined values may be provide provided and stored and/or displayed to a user. In some examples, the vascular resistance or stiffness is provided as a input signal to a feature extraction process 2914 and machine learning process 2916 for detection and or prediction of a subject's state at a process 2918, fed back in as additional features in machine learning algorithms, in a similar manner to that described above in reference to FIGS. 5 and 6.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. An apparatus comprising:
    a wearable sensor assembly configured to be attached to a subject at a peripheral vascular region, the wearable sensor assembly comprising:
        a piezoelectric pressure sensor configured to measure pressure data of the peripheral vascular region, wherein the piezoelectric sensor comprises a piezoelectric electrode structure positioned to measure the pressure data in response to movement of a blood vessel in the peripheral vascular region, and
        a pulse-oximetry sensor positioned to collect photoplethysmograph derived blood flow data of the blood vessel; and
    a signal processor configured to
        receive the pressure data from the piezoelectric pressure sensor,
        analyze the pressure data and output a pressure value,
        analyze the collected photoplethysmograph derived blood flow and output a photoplethysmograph blood flow value, using a model of pulse-oximetry sensor voltage output,
        compare the photoplethysmograph blood flow value with the pressure value to determine an elliptical fit, and
        based on the elliptical fit, extract an indicator of peripheral vascular resistance of the blood vessel, wherein the indicator of peripheral vascular resistance indicates vascular health and condition of the subject.

2. The apparatus of claim 1, wherein a signal processor is configured to
    receive raw pressure data from the piezoelectric sensor,
    filter the received raw pressure data, and
    perform signal decomposition on the filtered raw pressure data and output the pressure data for analysis and extraction.

3. The apparatus of claim 1, wherein the signal processor is configured to analyze the collected photoplethysmograph derived blood flow and output the photoplethysmograph blood flow value, $u_{PPG}$, according to:

$$u_{PPG}=K_{PPG}\int h_{PPG}*V_i dt = K_{PPG}\int h_{PPG}*\pi r_i^2 L_{PPG} dt,$$

where $K_{PPG}$ is a gain of the pulse-oximetry sensor, $h_{PPG}$ is a linear dynamic filter response, and $V_i$ is a volume of oxygenated blood in the vascular region.

4. The apparatus of claim 1, wherein the signal processor is configured to analyze the collected photoplethysmograph derived blood flow and output the photoplethysmograph blood flow value, $u_{PPG}$, according to:

$$u_{PPG}=K_{PPG}\int h_{PPG}*\pi r_i^2 L_{PPG} dt,$$

where $K_{PPG}$ is a gain of the piezoelectric pressure sensor, $h_{PPG}$ is a linear dynamic filter response,
$r_i$ is an inner radius of the blood vessel, and $L_{PPG}$ is a length of the blood vessel illuminated by the pulse-oximetry sensor.

5. The apparatus of claim 1, wherein the signal processor is configured to analyze the pressure data and output a pressure value, $u_{PVDF}$, according to:

$$u_{PVDF}=\int h_{PVDF}(t)*q(t)dt,$$

where $h_{pvdf}$ is a transfer function of the piezoelectric pressure sensor and where $q(t)$ is a charge amount measured by the piezoelectric pressure sensor.

6. The apparatus of claim 1, wherein to compare the photoplethysmograph blood flow value and the pressure value to determine the elliptical fit, the signal processor is configured to:
    develop an elliptical model of the pressure value versus the photoplethysmograph blood flow value;
    determine for a long chord of the elliptical model, a fixed model radius, Ls; and
    determine for the long chord of an experimentally obtained elliptical model, a model radius, Le.

7. The apparatus of claim 6, wherein the signal processor is configured to extract the indicator of vascular resistance of the blood vessel based on variation in amplitudes of the pressure value and the photoplethysmograph blood flow value represented by Ls and Le, respectively.

8. The apparatus of claim 6, wherein the signal processor is configured to extract the indicator of vascular resistance of the blood vessel based on variation of the pressure value versus the photoplethysmograph blood flow value using a hysteresis comparison measured by the elliptical model.

9. The apparatus of claim 1, further comprising a self-contained power source of the piezoelectric sensor and/or the photoplethysmography sensor in the wearable sensor assembly.

10. The apparatus of claim 1, wherein the signal processor is external to the wearable sensor assembly and communicatively connected the wearable sensor assembly through a wireless communication network or through an external wired connection.

11. The apparatus of claim 1, wherein the signal processor is configured to determine cardiac vascular power.

12. The apparatus of claim 11, wherein to determine cardiac vascular power, the signal processor is configured to:
    determine a charge response of the piezoelectric pressure sensor;
    determine a square of the charge response; and
    apply a piezoelectric sensor property factor to the square of the charge response, wherein the piezoelectric sensor property factor is a value that compensates for one or more of material properties of the piezoelectric sensor, dimensions of the piezoelectric sensor, an amount of deformation of the piezoelectric sensor, and combinations thereof.

13. The apparatus of claim 1, wherein the signal processor is configured to determine a radius of the blood vessel.

14. The apparatus of claim 1, wherein the wearable sensor assembly further comprises:
an additional piezoelectric pressure sensor configured to measure an absolute pressure data of the peripheral vascular region, and
wherein the signal processor is configured to
receive the absolute pressure data from the additional piezoelectric pressure sensor,
compare the absolutely data to the pressure data from the piezoelectric pressure sensor, and
determine an absolute blood pressure for the subject.

15. The apparatus of claim 1, wherein the signal processor is further configured to
determine an average pulse transit time (PTT) between the piezoelectric pressure sensor and the pulse-oximetry sensor over a sample period,
determine if a subsequent PTT deviates by more than a threshold amount from the average PTT, and
identify the subsequent PTT and corresponding pressure value and photoplethysmograph blood flow value as noise, if the subsequent PTT deviates by more than a threshold amount from the average PTT.

16. The apparatus of claim 1, wherein the signal processor is further configured to
determine an average pulse transit time (PTT) between the piezoelectric pressure sensor and the pulse-oximetry sensor over a sample period, and
determine a vascular mechanical stiffness for the blood vessel from the PTT.

17. The apparatus of claim 1, wherein the signal processor is configured to determine a radius of the blood vessel, $r_0$, according to:

$$\pi(\overline{R}+\delta R)^2 = 2\pi(r_o+\delta r_o)^2 + V_o - \gamma \delta p_o$$

where $\overline{R}$ is a nominal radius of the piezoelectric pressure sensor, $\delta R$ is a piezoelectric pressure sensor perturbation expression, $V_o$ is a nominal cross-sectional of the peripheral vascular region enclosed by the piezoelectric pressure sensor, excluding a cross-section area of a blood vessel, $\gamma$ is a measure of net intervening tissue compressibility for the peripheral vascular region, $\delta p_o$ is sensor pressure perturbation expression, and $\delta r_o$ is a blood vessel perturbation expression.

18. The apparatus of claim 1, wherein the signal processor is further configured to
compare the photoplethysmograph blood flow value with the pressure value using a state model, the state model configured to model at least one of physical properties of the wearable sensor assembly, properties of the vascular region, and properties of the blood vessel,
apply an extended Kalman filter to the comparison of the photoplethysmograph blood flow value with the pressure value using a state model, and
extract the indicator of peripheral vascular radius as the indicator of peripheral vascular resistance of the blood vessel.

19. The apparatus of claim 18, wherein the signal processor is further configured to
extract an indicator of peripheral vascular radius, vascular stiffness, blood pressure, or cardiac vascular power.

20. The apparatus of claim 18, wherein the signal processor is further configured to extract an indicator of peripheral vascular radius of the blood vessel, vascular stiffness of the blood vessel, blood pressure, or cardiac vascular power in response to a comparison of the photoplethysmograph blood flow value with the pressure value.

21. A therapeutic delivery system for administering a therapeutic treatment to a subject, the delivery system comprising:
the apparatus of claim 20; and
an administration system comprising a therapeutic delivery vehicle in communication with a therapeutic treatment processor that controls delivery of the therapeutic treatment to the subject, the therapeutic treatment processor being
(i) coupled to receive the indicator of the peripheral vascular resistance of the blood vessel, peripheral vascular radius of the blood vessel, vascular stiffness of the blood vessel, blood pressure, and/or cardiac vascular power, in a closed loop manner, and
(ii) implemented to determine instructions for administering the therapeutic treatment.

* * * * *